US010000881B2

(12) United States Patent
Morris et al.

(10) Patent No.: US 10,000,881 B2
(45) Date of Patent: Jun. 19, 2018

(54) METHOD FOR ANTIMICROBIAL FABRIC APPLICATION

(71) Applicant: Applied Silver, Inc., Hayward, CA (US)

(72) Inventors: William M. Morris, San Francisco, CA (US); Sean D. Morham, Napa, CA (US); David E. Brown, Danville, CA (US); Keith S. Copenhagen, Oakland, CA (US); Thomas B. Brezoczky, Los Gatos, CA (US)

(73) Assignee: Applied Silver, Inc., Hayward, CA (US)

( * ) Notice: Subject to any disclaimer, the term of this patent is extended or adjusted under 35 U.S.C. 154(b) by 0 days. days.

(21) Appl. No.: 14/460,262

(22) Filed: Aug. 14, 2014

(65) Prior Publication Data

US 2015/0159319 A1 Jun. 11, 2015

Related U.S. Application Data

(60) Provisional application No. 61/912,768, filed on Dec. 6, 2013.

(51) Int. Cl.
*B05D 1/18* (2006.01)
*D06F 39/02* (2006.01)
(Continued)

(52) U.S. Cl.
CPC .......... *D06F 39/022* (2013.01); *A01N 59/16* (2013.01); *B05D 1/18* (2013.01); *D06M 23/10* (2013.01); *B05D 5/00* (2013.01); *D06F 35/00* (2013.01)

(58) Field of Classification Search
CPC .................... B05D 1/18; B05D 5/00
See application file for complete search history.

(56) References Cited

U.S. PATENT DOCUMENTS 3,751,885 A   8/1973   McNeely
4,048,032 A   9/1977   Eibl
(Continued)

FOREIGN PATENT DOCUMENTS

CH   698955     12/2009
CN   1218009     6/1999
(Continued)

OTHER PUBLICATIONS

Liu et al., "Controlled Release of Biologically Active Silver from Nanosilver Surfaces," ACS Nano, 2010, pp. 6903-6913, vol. 4, No. 11.
(Continued)

*Primary Examiner* — David P Turocy
(74) *Attorney, Agent, or Firm* — McDonnell Boennen Hulbert & Berghoff LLP

(57) ABSTRACT

An antimicrobial supply system employs a process water supply and incorporates a metallic ion supply connected to the process water supply to provide a high ion concentrate to an output. A dilution reservoir is connected to the metallic ion supply output and has an input from the process water supply. A pump is connected to an output of the reservoir. A manifold connected to the pump provides a dilute concentrate to at least one washing system. An electronics control module is connected to a first flow controller between the process water supply and the metallic ion supply and a second flow controller between the metallic ion supply and the reservoir for dilution control establishing a desired metallic ion concentration.

21 Claims, 16 Drawing Sheets

(51) Int. Cl.
*A01N 59/16* (2006.01)
*D06M 23/10* (2006.01)
*B05D 5/00* (2006.01)
*D06F 35/00* (2006.01)

(56) References Cited

U.S. PATENT DOCUMENTS

| | | |
|---|---|---|
| 4,098,660 A | 7/1978 | Eibl et al. |
| 4,119,518 A | 10/1978 | Miller |
| 4,145,291 A | 3/1979 | Console et al. |
| 4,198,296 A | 4/1980 | Doumas et al. |
| 4,525,253 A | 6/1985 | Hayes et al. |
| 4,545,956 A | 10/1985 | Ciszewski et al. |
| 4,696,742 A | 9/1987 | Shimazaki |
| 4,710,282 A | 12/1987 | Chak et al. |
| 4,755,268 A | 7/1988 | Matsuo et al. |
| 4,933,870 A | 6/1990 | Chang |
| 4,995,975 A | 2/1991 | Jacquot et al. |
| 5,190,659 A | 3/1993 | Wang et al. |
| 5,281,312 A | 1/1994 | Woodside |
| 5,342,528 A | 8/1994 | Adachi et al. |
| 5,364,512 A | 11/1994 | Earl |
| 5,445,023 A * | 8/1995 | Reed .............. G01F 19/002 73/426 |
| 5,632,904 A | 5/1997 | Samad et al. |
| 5,765,403 A | 6/1998 | Lincoln et al. |
| 5,782,109 A | 7/1998 | Spriggs et al. |
| 5,787,537 A * | 8/1998 | Mannillo ............ D06F 39/006 210/639 |
| 5,843,284 A | 12/1998 | Waters et al. |
| 5,858,246 A | 1/1999 | Rafter et al. |
| 6,022,459 A | 2/2000 | Briggs et al. |
| 6,128,931 A | 10/2000 | Woods |
| 6,254,894 B1 | 7/2001 | Denkewicz, Jr. et al. |
| 6,267,885 B1 | 7/2001 | Briggs et al. |
| 6,303,039 B1 | 10/2001 | Back et al. |
| 6,398,927 B1 | 6/2002 | Merzhauser |
| 6,508,929 B1 | 1/2003 | Mercer |
| 6,514,406 B1 | 2/2003 | Katehis |
| 6,524,540 B1 | 2/2003 | Heinig, Jr. |
| 6,562,243 B2 | 5/2003 | Sherman |
| 6,634,048 B1 | 10/2003 | Hornung et al. |
| 6,641,829 B1 | 11/2003 | Green et al. |
| 6,761,827 B2 | 7/2004 | Coffey |
| 6,838,095 B2 | 1/2005 | Newman et al. |
| 6,929,740 B2 | 8/2005 | Hayes |
| 6,982,039 B1 | 1/2006 | Butkus et al. |
| 7,012,053 B1 | 3/2006 | Barnabus et al. |
| 7,152,759 B2 | 12/2006 | Walton |
| 7,322,065 B2 | 1/2008 | Kim et al. |
| 7,384,564 B2 | 6/2008 | Bo |
| 7,413,667 B1 | 8/2008 | Routberg et al. |
| 7,422,759 B2 | 9/2008 | Kepner et al. |
| 7,481,081 B2 * | 1/2009 | Hsu ................ D06F 33/02 68/17 R |
| 7,487,876 B2 | 2/2009 | Maeda |
| 7,540,966 B2 | 6/2009 | Costa et al. |
| 7,597,718 B2 | 10/2009 | Yoshikawa et al. |
| 7,617,704 B2 | 11/2009 | Iimori et al. |
| 7,624,601 B2 | 12/2009 | Ikemizu et al. |
| 7,708,896 B2 | 5/2010 | Ooe et al. |
| 7,807,199 B2 | 10/2010 | Allen et al. |
| 7,807,661 B2 | 10/2010 | Ylitalo et al. |
| 7,819,127 B1 | 10/2010 | Huffman |
| 7,882,647 B2 | 2/2011 | Ikemizu |
| 7,934,402 B2 | 5/2011 | Lee |
| 7,942,024 B2 | 5/2011 | Lee |
| 7,950,254 B2 | 5/2011 | Gray et al. |
| 7,972,519 B2 | 7/2011 | Koos et al. |
| 8,002,898 B2 * | 8/2011 | Schepers ............ A47L 15/0023 134/18 |
| 8,118,912 B2 | 2/2012 | Rodriguez et al. |
| 8,173,067 B2 | 5/2012 | Eldred |
| 8,239,990 B2 | 8/2012 | Lim et al. |
| 8,309,506 B2 | 11/2012 | Sunder et al. |
| 8,361,505 B1 | 1/2013 | Perry |
| 8,394,420 B2 | 3/2013 | Kepner et al. |
| 8,449,732 B2 | 5/2013 | Choi |
| 8,460,395 B2 | 6/2013 | Smulowitz |
| 8,563,447 B2 | 10/2013 | Canada |
| 8,641,947 B2 | 2/2014 | Schmuhl et al. |
| 8,729,008 B2 | 5/2014 | Begli et al. |
| 9,132,296 B2 | 9/2015 | Wingfield |
| 2001/0049846 A1 | 12/2001 | Guzzi et al. |
| 2002/0189954 A1 | 12/2002 | Miyazaki et al. |
| 2003/0170453 A1 | 9/2003 | Foss et al. |
| 2003/0190370 A1 | 10/2003 | Kim et al. |
| 2003/0196282 A1 | 10/2003 | Fyvie et al. |
| 2003/0230122 A1 | 12/2003 | Lee |
| 2004/0025263 A1 | 2/2004 | Kim et al. |
| 2004/0031764 A1 | 2/2004 | Heinig, Jr. |
| 2004/0205899 A1 | 10/2004 | Park et al. |
| 2004/0214495 A1 | 10/2004 | Foss et al. |
| 2005/0019568 A1 | 1/2005 | Foss et al. |
| 2005/0037057 A1 | 2/2005 | Schuette et al. |
| 2005/0095158 A1 | 5/2005 | Kirschner et al. |
| 2005/0118281 A1 | 6/2005 | Newman et al. |
| 2005/0155939 A1 | 7/2005 | Stadelmann |
| 2005/0188731 A1 | 9/2005 | Aouad |
| 2005/0194297 A1 | 9/2005 | Dorward |
| 2005/0224419 A1 | 10/2005 | Wien et al. |
| 2006/0110258 A1 | 5/2006 | Iimura et al. |
| 2006/0123562 A1 | 6/2006 | Ghosh et al. |
| 2006/0127457 A1 | 6/2006 | Buchalter |
| 2006/0130533 A1 | 6/2006 | Ooe et al. |
| 2006/0164093 A1 * | 7/2006 | Ooe ................ C02F 1/4606 324/432 |
| 2006/0265814 A1 | 11/2006 | Ritter |
| 2007/0004300 A1 | 1/2007 | Kreider et al. |
| 2007/0044820 A1 | 3/2007 | Chan et al. |
| 2007/0045176 A1 | 3/2007 | Chandra et al. |
| 2007/0134301 A1 | 6/2007 | Ylitalo et al. |
| 2007/0163097 A1 | 7/2007 | Metcalfe et al. |
| 2007/0175833 A1 | 8/2007 | Ikeboh et al. |
| 2007/0243380 A1 | 10/2007 | Vegad et al. |
| 2007/0243781 A1 | 10/2007 | Chou |
| 2008/0016919 A1 | 1/2008 | Lee |
| 2008/0023385 A1 | 1/2008 | Baker, Jr. et al. |
| 2008/0041117 A1 | 2/2008 | Lee |
| 2008/0085326 A1 | 4/2008 | Ruan |
| 2008/0131471 A1 | 6/2008 | Kolbe et al. |
| 2008/0217807 A1 | 9/2008 | Lee et al. |
| 2008/0248075 A1 | 10/2008 | Brambilla et al. |
| 2008/0256719 A1 | 10/2008 | Radev |
| 2008/0299006 A1 | 12/2008 | Ikemizu |
| 2008/0302713 A1 | 12/2008 | Patrick |
| 2009/0000040 A1 * | 1/2009 | Ikemizu ............ D06F 35/003 8/158 |
| 2009/0104239 A1 | 4/2009 | Parsons et al. |
| 2009/0181592 A1 | 7/2009 | Dugan |
| 2009/0193593 A1 * | 8/2009 | Kirigakubo .......... C11D 3/0068 8/142 |
| 2009/0218266 A1 | 9/2009 | Sawafta et al. |
| 2009/0259157 A1 | 10/2009 | Thomas |
| 2010/0000268 A1 | 1/2010 | Kohne |
| 2010/0047321 A1 * | 2/2010 | Sandford ............ A01N 59/16 424/443 |
| 2010/0050872 A1 | 3/2010 | Lee |
| 2010/0102002 A1 | 4/2010 | O'Brien et al. |
| 2010/0116689 A1 | 5/2010 | Greene et al. |
| 2010/0140185 A1 | 6/2010 | Hill |
| 2010/0183739 A1 | 7/2010 | Newman |
| 2010/0193449 A1 | 8/2010 | Shang et al. |
| 2010/0243432 A1 | 9/2010 | Ikemizu |
| 2011/0017609 A1 | 1/2011 | Choi |
| 2011/0094972 A1 | 4/2011 | King et al. |
| 2011/0100838 A1 | 5/2011 | Kim et al. |
| 2011/0120921 A1 | 5/2011 | Kim |
| 2011/0139632 A1 | 6/2011 | Beringer et al. |
| 2011/0120423 A1 | 7/2011 | Barry et al. |
| 2011/0224120 A1 | 9/2011 | Meine et al. |
| 2011/0262556 A1 | 10/2011 | Holladay et al. |
| 2011/0297609 A1 | 12/2011 | Hu |
| 2012/0003326 A1 | 1/2012 | Meine et al. |

(56) References Cited

U.S. PATENT DOCUMENTS

| | | |
|---|---|---|
| 2012/0055862 A1 | 3/2012 | Parekh et al. |
| 2012/0091070 A1 | 4/2012 | Sjaunta et al. |
| 2012/0187052 A1 | 7/2012 | Elliott |
| 2012/0192363 A1 | 8/2012 | King |
| 2012/0213665 A1 | 8/2012 | Bik et al. |
| 2013/0022686 A1 | 1/2013 | Rademan et al. |
| 2013/0281345 A1 | 10/2013 | Burkinshaw et al. |
| 2013/0327419 A1 | 12/2013 | Morham |
| 2014/0202943 A1 | 7/2014 | Pradeep et al. |
| 2014/0369953 A1 | 12/2014 | Purschwitz et al. |
| 2015/0047718 A1 | 2/2015 | Brown et al. |
| 2015/0159314 A1 | 6/2015 | Morham et al. |
| 2015/0159319 A1 | 6/2015 | Morris et al. |

FOREIGN PATENT DOCUMENTS

| | | |
|---|---|---|
| CN | 1558016 | 12/2004 |
| CN | 1671911 | 9/2005 |
| CN | 2725278 | 9/2005 |
| CN | 2753774 | 1/2006 |
| CN | 2780804 | 5/2006 |
| CN | 200984347 | 12/2007 |
| CN | 101411958 | 4/2008 |
| CN | 201056507 | 5/2008 |
| CN | 101307555 | 11/2008 |
| CN | 201254480 | 6/2009 |
| CN | 101670123 | 3/2010 |
| CN | 101731269 | 6/2010 |
| CN | 101863581 | 10/2010 |
| CN | 101864670 | 10/2010 |
| CN | 101926363 | 12/2010 |
| CN | 101967025 | 2/2011 |
| CN | 201737797 | 2/2011 |
| CN | 201738163 | 2/2011 |
| CN | 101991870 | 3/2011 |
| CN | 201791121 | 4/2011 |
| CN | 201873556 | 6/2011 |
| CN | 201902711 | 7/2011 |
| CN | 202021117 | 11/2011 |
| CN | 202023990 | 11/2011 |
| CN | 202036069 | 11/2011 |
| CN | 102330844 | 1/2012 |
| CN | 202121806 | 1/2012 |
| CN | 102421295 | 4/2012 |
| CN | 102535114 | 7/2012 |
| CN | 202386643 | 8/2012 |
| CN | 202390678 | 8/2012 |
| CN | 102666397 | 9/2012 |
| CN | 202410344 | 9/2012 |
| CN | 202430491 | 9/2012 |
| CN | 102781814 | 11/2012 |
| DE | 19853193 | 5/2000 |
| DE | 102007034215 | 5/2008 |
| EP | 028782 | 11/1987 |
| EP | 1296895 | 4/2003 |
| EP | 1334073 | 8/2003 |
| EP | 1600545 | 11/2005 |
| EP | 1785518 | 5/2007 |
| EP | 1 983 085 A1 | 10/2008 |
| EP | 2045389 | 4/2009 |
| EP | 2461676 | 6/2012 |
| EP | 2499916 | 9/2012 |
| EP | 2513370 | 10/2012 |
| EP | 2544804 | 1/2013 |
| EP | 2674523 | 12/2013 |
| GB | 2298858 | 3/1995 |
| GB | 2419590 | 5/2006 |
| JP | H0560721 | 3/1993 |
| JP | 2001025772 | 1/2001 |
| JP | 2001062458 | 3/2001 |
| JP | 2001066090 | 3/2001 |
| JP | 2001276484 | 10/2001 |
| JP | 2001340281 | 12/2001 |
| JP | 2002113288 | 4/2002 |
| JP | 2004057423 | 2/2004 |
| JP | 2004105692 | 4/2004 |
| JP | 2004313752 | 11/2004 |
| JP | 2004346024 | 12/2004 |
| JP | 2005098606 | 4/2005 |
| JP | 2005261830 | 9/2005 |
| JP | 2005296671 | 10/2005 |
| JP | 2007061757 | 3/2007 |
| JP | 2007167785 | 7/2007 |
| JP | 2008009287 | 5/2008 |
| JP | 2008183283 | 8/2008 |
| JP | 2008220450 | 9/2008 |
| JP | 2008279056 | 11/2008 |
| JP | 2009017907 | 1/2009 |
| JP | 2009039320 | 2/2009 |
| JP | 2010136738 | 6/2010 |
| JP | 2010136739 | 6/2010 |
| JP | 2010194484 | 9/2010 |
| JP | 2012161728 | 8/2012 |
| JP | 2014176448 | 9/2014 |
| KR | 1990069099 | 9/1999 |
| KR | 20000037120 | 7/2000 |
| KR | 20020012369 | 2/2002 |
| KR | 20020074306 | 9/2002 |
| KR | 20040085107 | 10/2004 |
| KR | 20040093957 | 11/2004 |
| KR | 20050004614 | 1/2005 |
| KR | 20050004616 | 1/2005 |
| KR | 20050004618 | 1/2005 |
| KR | 20050004620 | 1/2005 |
| KR | 20050004621 | 1/2005 |
| KR | 20050004623 | 1/2005 |
| KR | 20050004625 | 1/2005 |
| KR | 20050004626 | 1/2005 |
| KR | 20050065718 | 6/2005 |
| KR | 20050068357 | 7/2005 |
| KR | 20050089257 | 9/2005 |
| KR | 20070028012 | 3/2007 |
| KR | 100736819 | 7/2007 |
| KR | 100818561 | 4/2008 |
| KR | 20080075694 | 8/2008 |
| KR | 20090001293 | 1/2009 |
| KR | 20090090501 | 8/2009 |
| KR | 20110062719 | 6/2011 |
| KR | 20110075870 | 7/2011 |
| KR | 20120000652 | 1/2012 |
| KR | 101430906 | 8/2014 |
| MD | 2940 | 12/2005 |
| RU | 2135417 | 8/1999 |
| RU | 2182128 | 5/2002 |
| RU | 2193528 | 11/2002 |
| RU | 2264990 | 11/2005 |
| RU | 2324026 | 5/2008 |
| RU | 2373156 | 11/2009 |
| RU | 2381182 | 2/2010 |
| TW | I252268 | 4/2006 |
| TW | 200902790 | 1/2009 |
| TW | 201013008 | 4/2010 |
| TW | 201127948 | 8/2011 |
| TW | 201138638 | 11/2011 |
| UA | 22673 | 4/2007 |
| WO | 1999039749 | 8/1999 |
| WO | 2002036499 | 5/2002 |
| WO | 2003051780 | 5/2003 |
| WO | 2004104153 | 12/2004 |
| WO | 2006014080 | 1/2006 |
| WO | 2006129982 | 12/2006 |
| WO | 2007057077 | 5/2007 |
| WO | 2008075992 | 6/2008 |
| WO | 2011015429 | 2/2011 |
| WO | 2011067748 | 6/2011 |
| WO | 2011073697 | 6/2011 |
| WO | 2011110550 | 9/2011 |
| WO | 2011126395 | 10/2011 |
| WO | 2011139835 | 11/2011 |
| WO | 2012025943 | 3/2012 |
| WO | 2012031853 | 3/2012 |
| WO | 2012059992 | 5/2012 |
| WO | 2012077122 | 6/2012 |
| WO | 2012095665 | 7/2012 |

(56) References Cited

FOREIGN PATENT DOCUMENTS

| WO | 2012095828 | 7/2012 |
| WO | 2012107422 | 8/2012 |
| WO | 2012140520 | 10/2012 |
| WO | 2012142025 | 10/2012 |
| WO | 2012150506 | 11/2012 |
| WO | 2012155269 | 11/2012 |
| WO | 2014196881 | 12/2014 |
| WO | 2015001870 | 1/2015 |
| WO | 2015084568 | 6/2015 |
| WO | 2015084569 | 6/2015 |

OTHER PUBLICATIONS

Mitrano et al., "Presence of Nanoparticles in Wash Water from Conventional Silver and Nano-silver Textiles," ACS Nano, 2014, pp. 7208-7219, vol. 8, No. 7.

Putro et al., "Silver Nano Perfume Ejector to Destroy Bacteria for Clothes," AASIC, 2013, pp. 72-75.

\* cited by examiner

METHOD FOR ANTIMICROBIAL FABRIC APPLICATION

REFERENCE TO RELATED APPLICATIONS

This application relies on the priority of U.S. Provisional Application Ser. No. 61/912,768 filed on Dec. 6, 2013 having a common assignee with the present application, the disclosure of which is incorporated herein by reference. This application is copending with application Ser. No. 14/460,287 entitled ANTIMICROBIAL FABRIC APPLICATION SYSTEM filed concurrently herewith, the disclosure of which is incorporated herein by reference.

BACKGROUND OF THE INVENTION

Field

The present invention is in the technical field of antimicrobial treatment of fabrics and textile materials. More particularly, the present invention provides a system providing metallic ion generation and dilution, in desired concentrations, for batch storage and entrainment in a flow for use in antimicrobial treatment of fabrics and a method for controlled introduction of the antimicrobial agent into the textile.

Related Art

Shortcomings of existing antimicrobial treatments can lead to stain and odor causing bacteria build-up, mold and mildew as well as the spread of infection through direct contact, airborne disease and waterborne disease. These diseases can be acquired by their victims from contacting contaminated surfaces, breathing air containing pathogens, or drinking pathogen containing water. Contamination of fabrics or textiles in uniforms, surgical scrubs, sheets, blankets, napkins, table cloths and similar materials by microbial pathogens can contribute to spread of disease.

Prior art antimicrobial treatments do not provide effective lasting antimicrobial benefit after the treatment has been administered. Existing antimicrobial treatments can also lead to immunization of evolved pathogens to the respective treatment. Such immunization of evolved pathogens can result in infections which cannot be treated with the conventional treatments that caused the pathogens to become immune.

Enterprises which specifically have problems with microbial issues ranging from bacterial odor through the spread of infectious diseases include, but are not limited to: the cruise line industry, hotel and gaming, professional sports teams, health and fitness clubs, nursing homes, households and hospitals. Healthcare facilities currently have a growing problem with immunized pathogens being virtually untreatable with conventional methods. With such hospital infections, the harmful microbes are often carried in the linens and clothing provided by the hospital. Once hospital textiles have been laundered, they are susceptible to recontamination by microbes and pathogens. Pathogens carried by these textiles can infect hospital patients, health care workers and even cause death. Since almost every patient spends the majority of his or her time in bed, in a gown, between the sheets, this linen environment is the core of the overall hospital environment for the patient, and a primary site in the battle against infection. In other environments such as households or Cruise Ship industries, textiles are ubiquitous, including napkins, tablecloths, aprons, uniforms, towels, and robes.

In the healthcare field antimicrobial fabrics have been employed in which an antimicrobial ingredient is imparted into the threads or fibers during fiber or textile manufacturing. The fibers are embedded, dipped, soaked, or coated with antimicrobial agent during the manufacturing process. However, efficacy declines over time as the antimicrobial agent in the fabric is washed away and never restored.

These methods are not satisfactory for the market. In addition to the efficacy/performance issues listed above and because the textiles are manufactured to already include the beneficial antimicrobial agent such as silver, these products require linen providers to make a large upfront capital investment to purchase new, impregnated linen inventory. Inventory replacement can cost millions of dollars for large industrial laundering businesses. Additionally, the linen's antimicrobial efficacy steadily degrades over time. After each use and wash, the antimicrobial feature is diminished, causing effectiveness to decrease over time. Further, the products are aesthetically unpleasing and uncomfortable to the touch. Linen providers have reported that silver-embedded fabrics can often exhibit an off-white discoloration and are difficult to press.

It is therefore desirable to provide an antimicrobial treatment system which may be employed directly in water supply systems to provide efficacious antimicrobial action in order to transform ordinary textile materials/products into lasting active antimicrobial entities.

SUMMARY OF THE INVENTION

The present embodiment disclosed herein provides an antimicrobial textile treatment system which employs a process water supply. A metallic ion supply provides a high ion concentrate to an output. A dilution reservoir is connected to the metallic ion supply output and has an input from the process water supply. A dosing pump connected to an output of the reservoir. A manifold is connected to the pump providing a dilute concentrate to at least one washing system. An electronics control module is connected to a first flow controller between the process water supply and the dilution reservoir and a second flow controller between the metallic ion supply output and the reservoir.

BRIEF DESCRIPTION OF THE DRAWINGS

These and other features and advantages of the present invention will be better understood by reference to the following detailed description of exemplary embodiments when considered in connection with the accompanying drawings wherein.

DETAILED DESCRIPTION OF THE INVENTION

Figure 1:
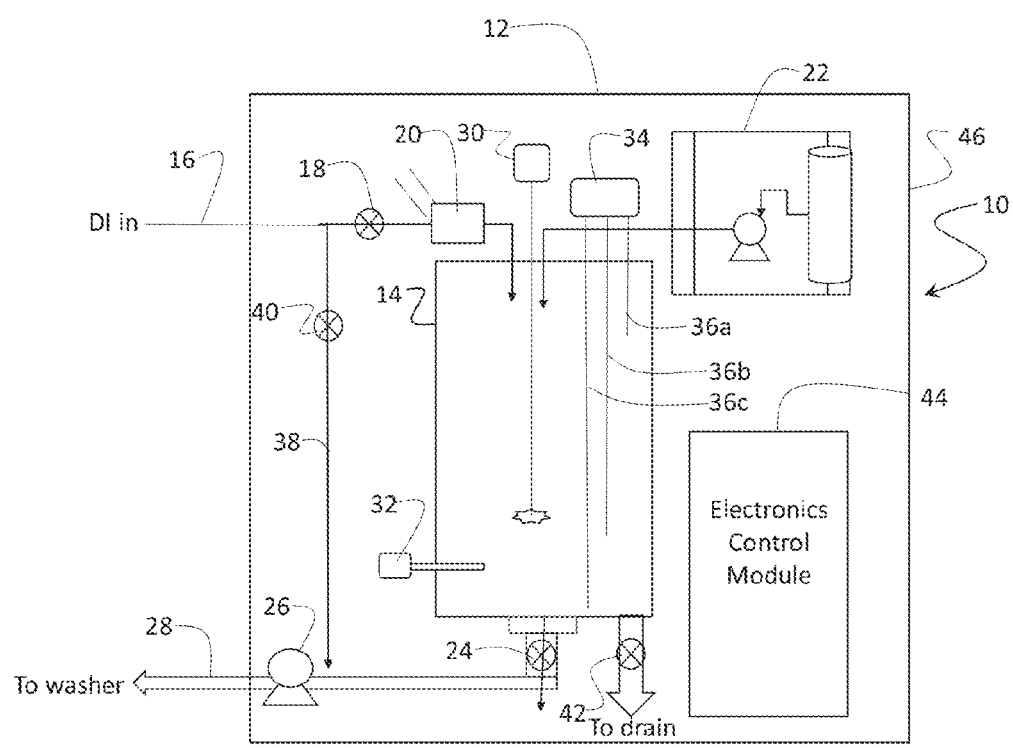
FIG. 1 is a block diagram representation of the concentrate supply and dilution system.

The embodiments disclosed herein provide a system for generation and batch dilution of metallic ions for use as an antimicrobial agent in processes such as commercial washing systems to treat textiles. The terms fabric, linen and textile are used interchangeably herein. Referring to the drawings, FIG. 1 shows a concentrate supply and dilution system 10 which is housed in a cabinet 12. The system 10 incorporates an addition column 14 as a dilution reservoir which receives deionized (DI) water through a DI inlet 16 under control of a DI solenoid valve 18. In exemplary embodiments, the addition column 14 may range in size from 0.5-5 L depending on the volumes of the commercial washing system components. An aeration device 20 aerates the incoming DI water flow to provide a desired $CO_2$ concentration in the DI water for enhanced conductance measurements, as will be described subsequently. The addition column 14 receives concentrated antimicrobial agent for dilution from a concentrate supply system 22, described in greater detail subsequently. A solenoid dosing valve 24 controls delivery of antimicrobial agent from the addition column and a dosing pump 26 administers desired amounts of antimicrobial agent from the addition column to a supply outlet 28 for use in a commercial washing system as will be described subsequently. A mixer 30 is employed to maintain an even distribution of DI water and antimicrobial agent in the addition column 14. A conductivity measurement probe 32 provides concentration measurement. A level probe system 34 having an overflow high level sensor 36a, a dose level sensor 36b and a reserve level sensor 36c allows quantity measurement in the addition column 14 for process control. A DI flush line 38 with a flush solenoid valve 40 provides DI water flush of the lines to the washer. A solenoid drain valve 42 is provided to drain the addition column 14. Control of the solenoid valves, mixer and concentrate supply system is accomplished through an electronics control module 44 which receives data input from the conductivity measurement probe 32 and the level probe system 34. An access panel 46 is provided in the cabinet 12 for replacement of concentrate canisters in the concentrate supply system 22.

Figure 2A:
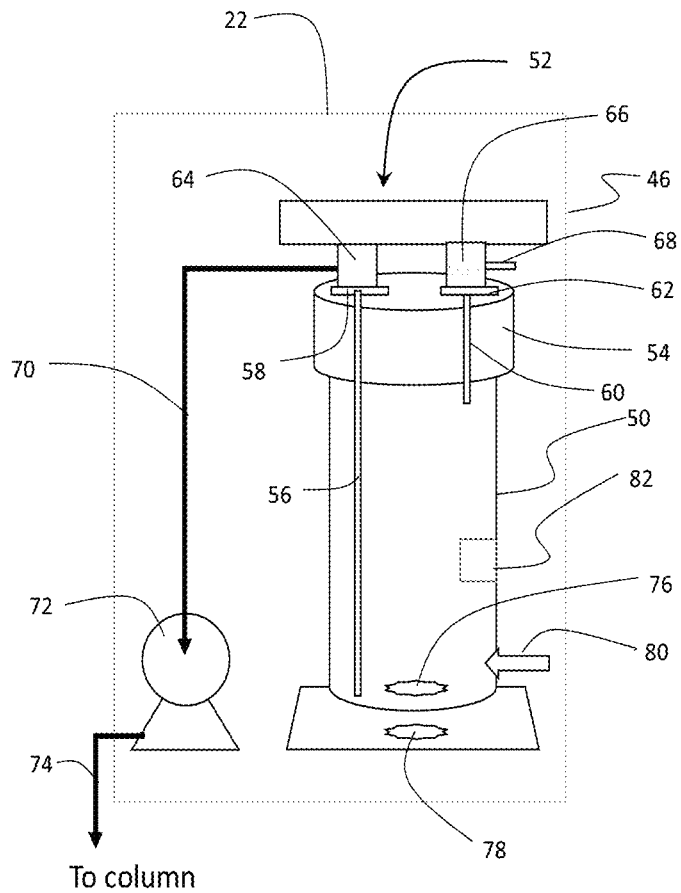
FIG. 2A is a detailed block diagram of a concentrate supply system.

Details of the concentrate supply system 22 are shown conceptually in FIG. 2A. A concentrate bottle or canister 50 is connectable into a receiver 52 for extraction of concentrated antimicrobial agent contained in the canister. For the embodiments described herein, a metallic silver solution is employed as the antimicrobial agent and may be compounded by employing a selected one of the following processes.

Silver nitrate or silver acetate may be dissolved in deionized water to reach a concentration of up to 1000 g Ag/L solution and stored at room temperature. Silver oxide may be dissolved in dilute nitric acid in the absence of carbon dioxide to a concentration of 25 ppm. For either of these solutions the canister 50 may be a clear container (preferably glass, but polypropylene or similar plastics may be employed).

Silver chloride may to be dissolved in 30% ammonium chloride to a concentration of 3000 g Ag per L solution. Silver Carbonate may be dissolved in dilute nitric acid to a concentration greater than its solubility in pure water of 0.0032 g/100 mL. These solutions are light sensitive (especially UV/sunlight). The canister 50 must therefore be opaque.

Silver sulfate is miscible in sulfuric acid. Silver sulfate can also be dissolved in water up to 0.79 g/100 mL. Silver powder with a particle size of approximately 2 um may be dissolved in dilute nitric acid to a final concentration equivalent to silver nitrate and stored at no lower than room temperature. The canister 50 for either of these solutions may be clear.

The canister 50 incorporates a sealed lid 54 to contain the metallic silver solution as a leak-proof container. A dip tube 56 for extraction of the solution extends from a first quick connect 58, shown integrated in the lid 54 for the embodiment in the drawings. A vent tube 60 extends from a second quick connect 62. The receiver 52 includes a first mating quick connect 64 to engage the dip tube quick connect 58 and a second mating quick connect 66 to engage the vent tube quick connect 62. A vent line 68 extends from the second mating quick connect 66 for venting the canister 50. A feed line 70 extends to the dip tube 56 through connection to the first mating quick connect 64 for delivery of ionic silver solution. A metering pump 72 is connected to the feed line 70 for delivery of the concentrated metallic silver solution to the addition column 14 through conduit 74. In exemplary embodiments, the metering pump is a precision adjustable pump such as an "STH" Low Flow Miniature OEM Pump available from Fluid Metering, Inc., 5 Aerial Way, Suite 500 Syosset, N.Y. 11791. Mixing capability for the canister 50 is employed to maintain a consistent solution of metallic silver concentrate in the canister. For the embodiment shown, a magnetic mixing spinner 76 is contained within the canister 50 and the receiver includes a magnetic driver 78 to activate the mixing spinner. In alternative embodiments, a connected stirring device or a vibratory mixer may be employed. A level indicator 80 is incorporated in the canister 50 to enable an empty warning system which may include bottle change frequency monitoring. Detection methods in the level indicator 80 may include ultrasonic, electro-optic, piezo-resonant, proximity or pressure. An identification element 82 is associated with the canister 50 for identification. A bar code label or similar device with a corresponding scanner may be employed or the identification element may incorporate on-board memory device such as an iButton available from Maxim Integrated. Inc., San Jose, Calif. (see http:/www.maximintegrated.com/products/ibutton/ibuttons/) that interfaces with the electronics module to carry out desired system functions. The memory device shall be used to track the canister 50 as inventory item, provide process & product trace-ability and shall enable the concentrate supply system 22 to operate, for example provide functional lock-out of operation without an acknowledged canister.

An exemplary embodiment of a receiver structure and associated concentrate container is shown in FIGS. 2B-2I.

Figure 2B:
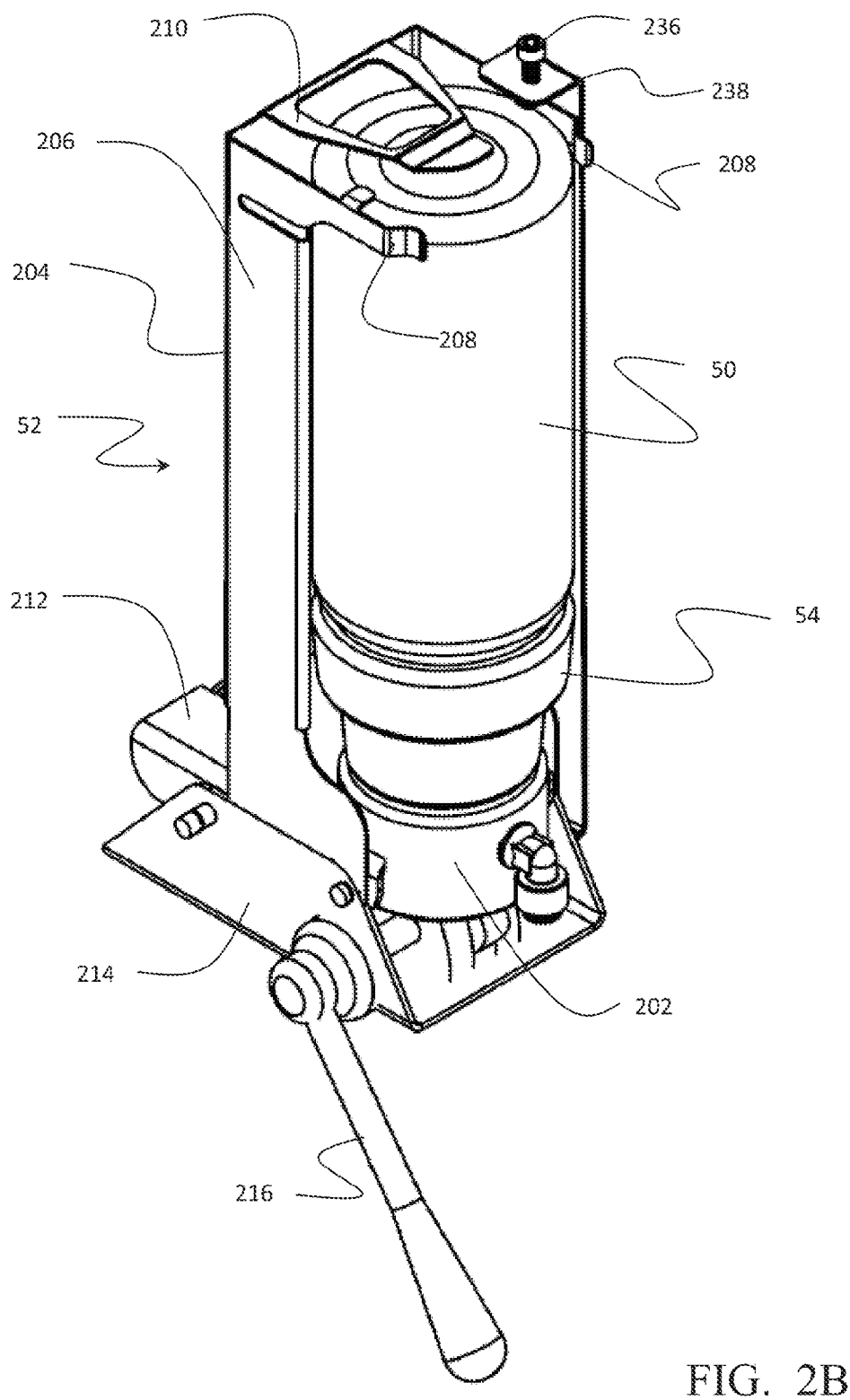
FIG. 2B is a pictorial view of an embodiment implementing the replaceable concentrate container with a receiver structure in a first installation position.

As seen in FIG. 2B, canister 50 is mounted in receiver 52 in an inverted position with sealed lid 54 engaging a connection element 202. The receiver includes a supporting structure 204 having vertical support arms 206 with lateral spring elements 208 and vertical spring element 210 to support and restrain the canister 50. A rotating cradle 212 supports the connection element 202. A base 214 engages the rotating cradle 212 and incorporates an activation handle 216. Upon activation of the supporting structure for fluid interconnection of the canister 50, as will be described in greater detail subsequently, concentrate from the canister 50 is fed through fitting 218 to the feed line 70 for distribution of the ionic silver solution as described with respect to FIG. 2A.

Figure 2C:
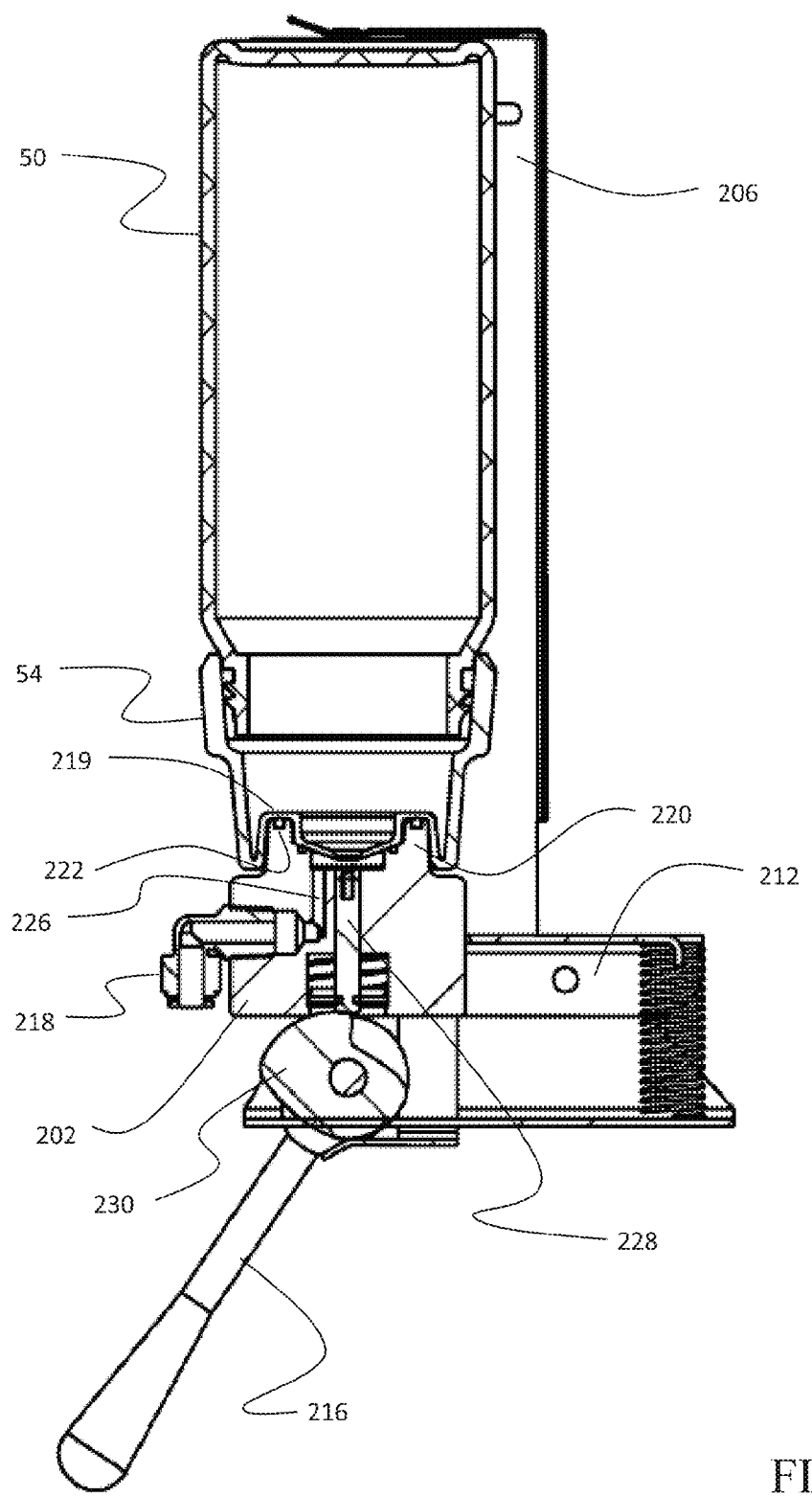
FIG. 2C is a side section view of the embodiment of FIG. 2B in the first position.
Figure 2D:
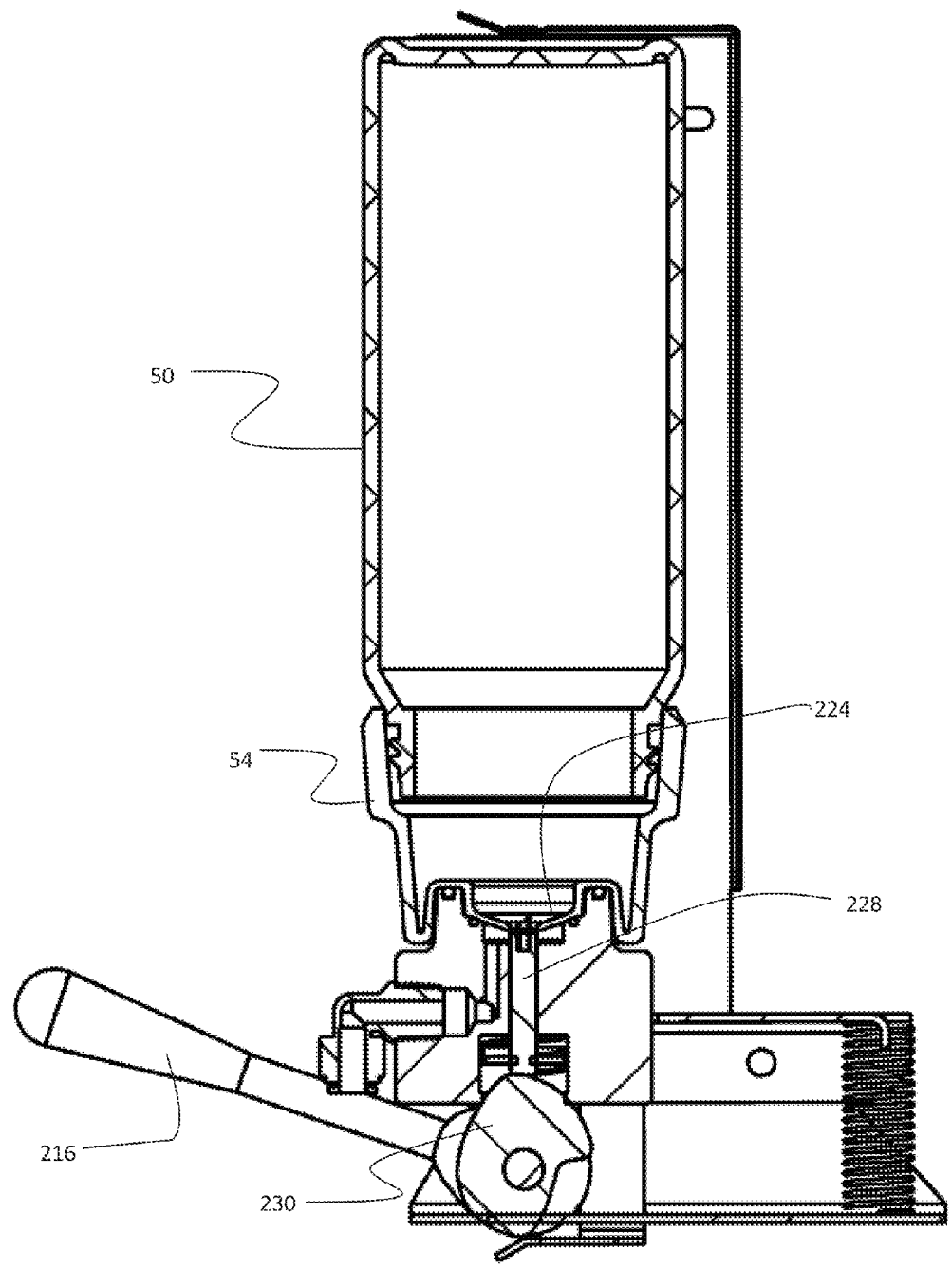
FIG. 2D is a side section view of the embodiment of FIG. 2B with the actuation handle of the receiver structure in motion for piercing of the concentrate container.
Figure 2E:
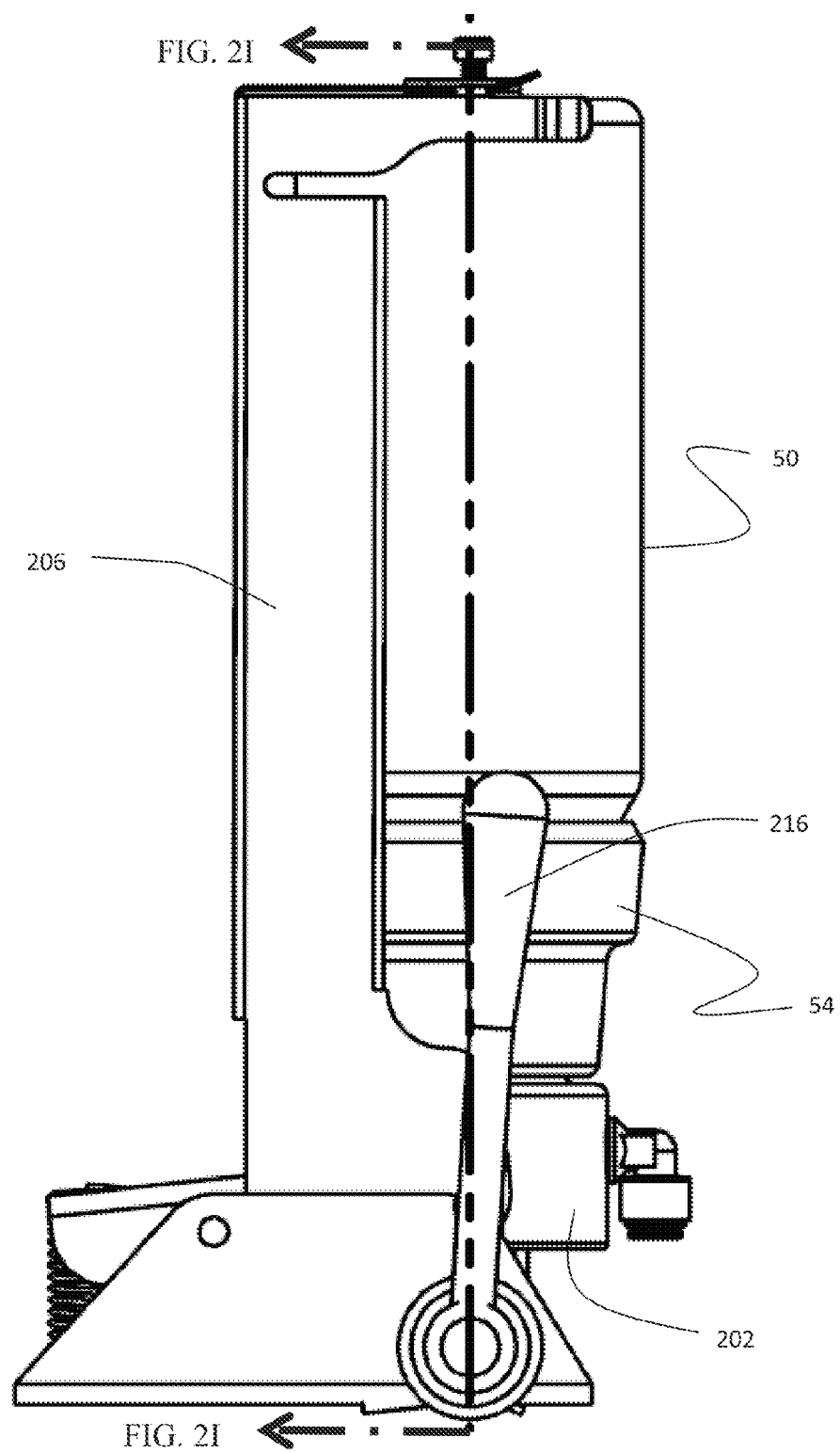
FIG. 2E is a side view showing the receiver structure and concentrate container in the in use position.
Figure 2F:
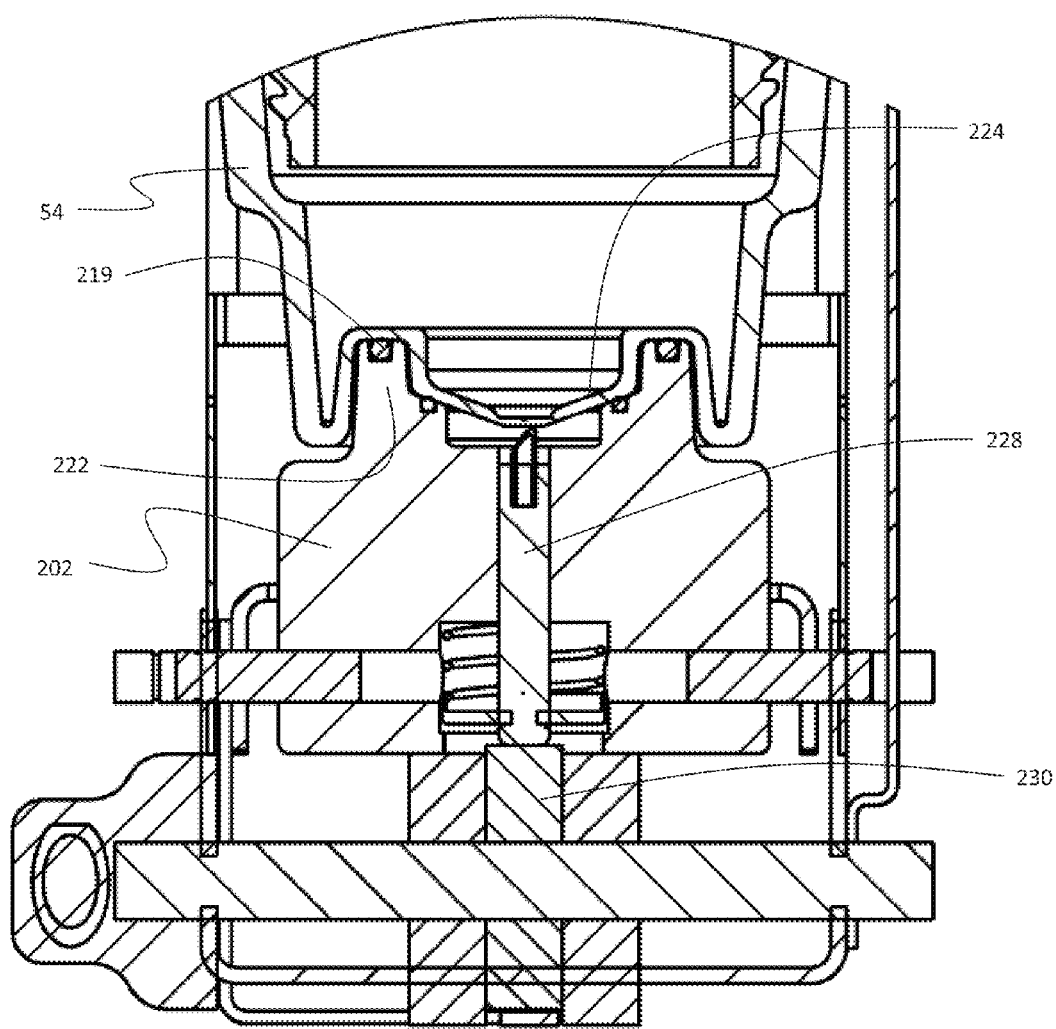
FIG. 2F is a front section detailed view of the container piercing system in the installation position.

As seen in FIGS. 2C and 2F, lid 54 incorporates an annular relief 219 which is received in an annular crown 220 on the connection element 202 to support the container and lid in the receiver. An o-ring seal 222 or similar sealing arrangement provides a seal between the relief 218 and the crown 220. A pierceable nipple 224 in the lid 54 is received within the crown 220 for communication with a feed conduit 226 terminating in the fitting 218. A piercing pin 228 is reciprocally mounted in the connection element 202 and is activated by a cam 230 interconnected to the activation handle 216. As shown in FIG. 2C with the handle in the "down" position for insertion of the container 50, the container is inserted in the receiver with the lid 54 engaged by the crown 220 on the connection element 220. The piercing pin 228 is retracted at the bottom of travel and the rotating cradle 212 is in a lowered position.

Figure 2G:
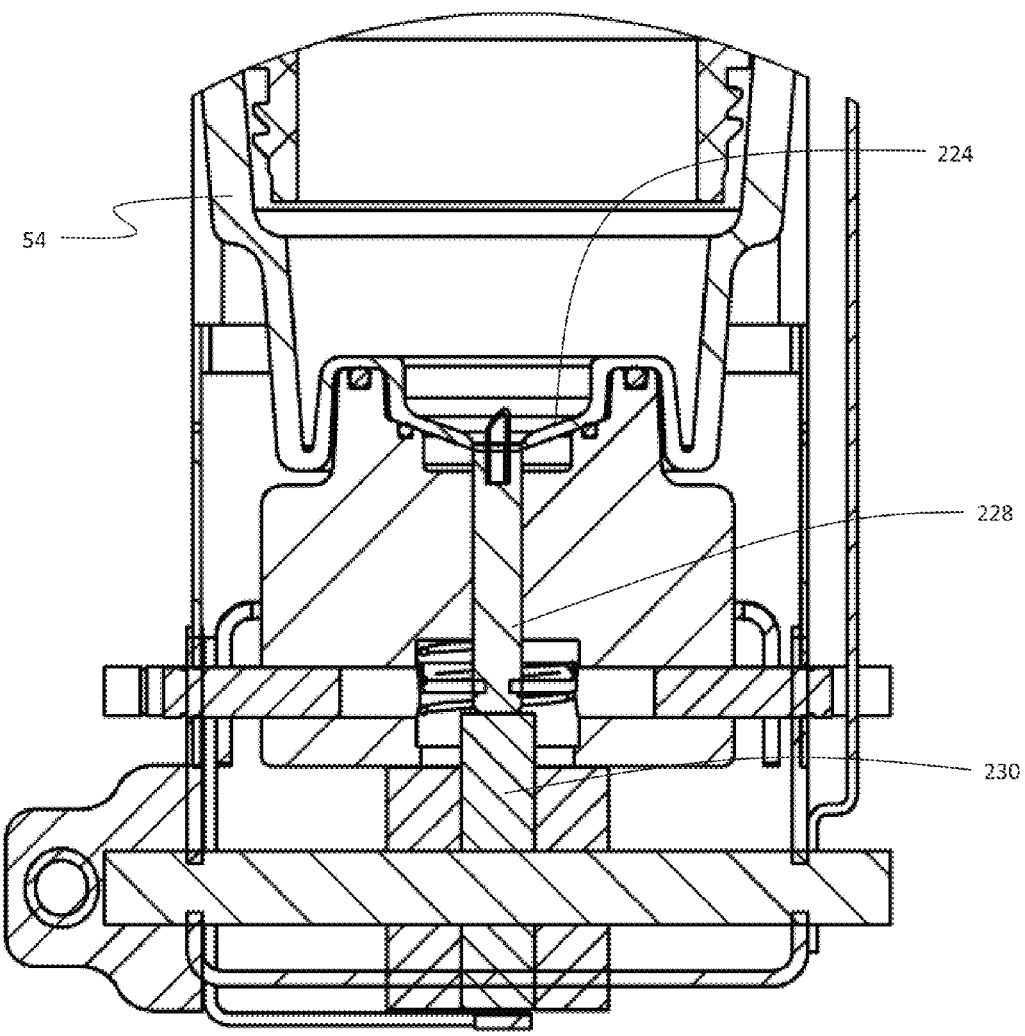
FIG. 2G is a front section detailed view of the container piercing system in the piercing position.
Figure 2H:
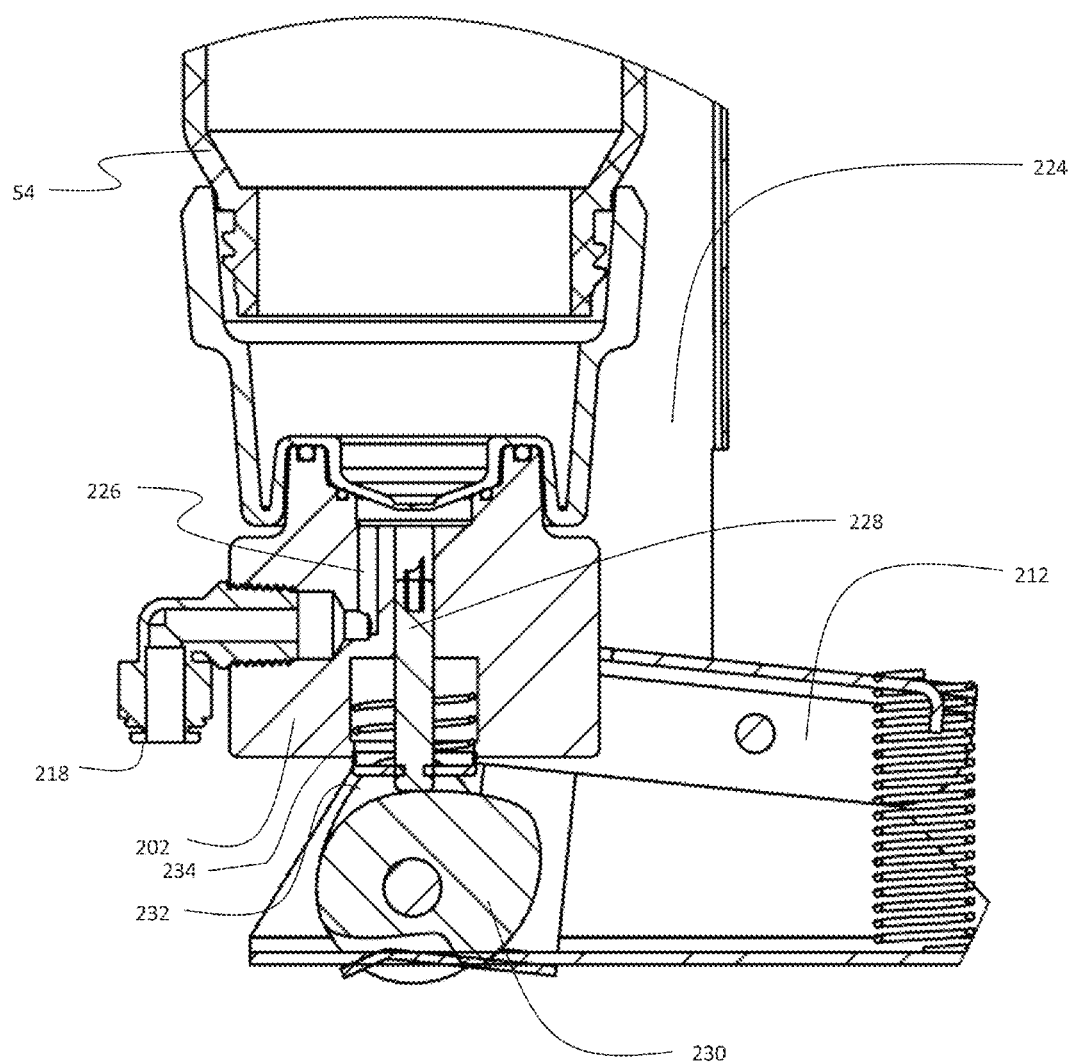
FIG. 2H is a front section detailed view of the container piercing system in the in use position.
Figure 2I:
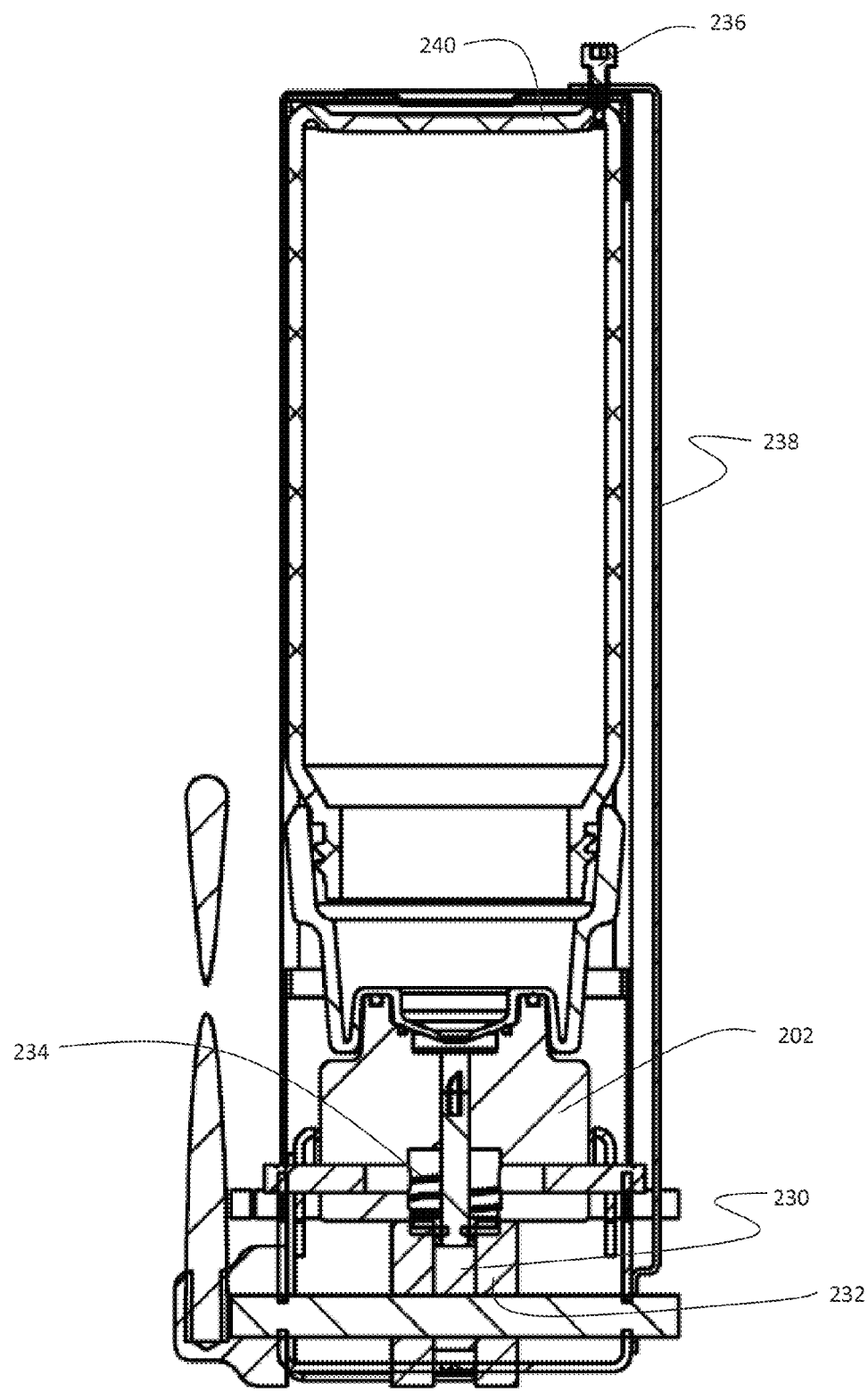
FIG. 2I is a front section view of the container piercing system in the in use position.

Upon an initial portion of rotation of the activating handle 216 as shown in FIGS. 2D and 2G, cam 230 is rotated to cause the cam lobe to reciprocate piercing pin 228 upward to contact and pierce the nipple 224 in the lid 54 of container 50. Upon continued rotation of the activating handle 216 to an "up" position as shown in FIGS. 2E and 2H, cam 230 has further rotated the lobe past piercing pin 228 allowing the pin to retract thereby placing the pierced container nipple 219 in fluid communication through conduit 226 to fitting 218. A second cam 232, best seen in FIG. 2I, is rotated by the handle 216 for contact to urge connection element 202 upward supported by rotating cradle 212. For the embodiment shown, a spring 234 interengages the second cam 232 and connection element 202. As shown in FIG. 2I, upon elevation of the container 50 by the connection element 202 and rotating cradle 212, a vent pin 236 restrained by a support column 238 is engaged to pierce the container wall 240 thereby venting the container for flow of concentrate.

Referring to both FIGS. 1 and 2A, standard operation of the concentrate supply and dilution system 10 for delivery of antimicrobial agent to a wash system is accomplished by opening column DI fill solenoid 18 and fill the addition column 14 until high level probe 36a is triggered. Metered addition of concentrate from the canister 46 is accomplished using precision metering pump 72 into the column 14. The conductance level probe 32 is de-energized and mixing is accomplished using mixer 30. The conductance level probe 32 is then activated for measurement to confirm the desired concentration of antimicrobial agent has been achieved. Dosing of diluted concentrate from the addition column 14 to the washer is then accomplished by opening the dosing solenoid valve 24 and turning on the dosing pump at a predetermined speed so that the dose is administered a predetermined dosing period, as indicated by the dose-level probe 36b dis-engagement from the solution. In exemplary embodiments the dosing period is 20-30 seconds. It may be desirable to vary the dosing rate during a dosing period. The dosing period is established to ensure uniformity of silver uptake in the textiles. The solenoid dosing valve is then closed and the dosing pump turned off. Flushing of the dosing pump and line to washer is then accomplished by opening the DI dosing line flush valve 40 and turning on the dosing pump. Upon completion of the line flush, the DI dosing line flush valve 40 is closed and the dosing pump 26 is turned OFF.

Figure 3:
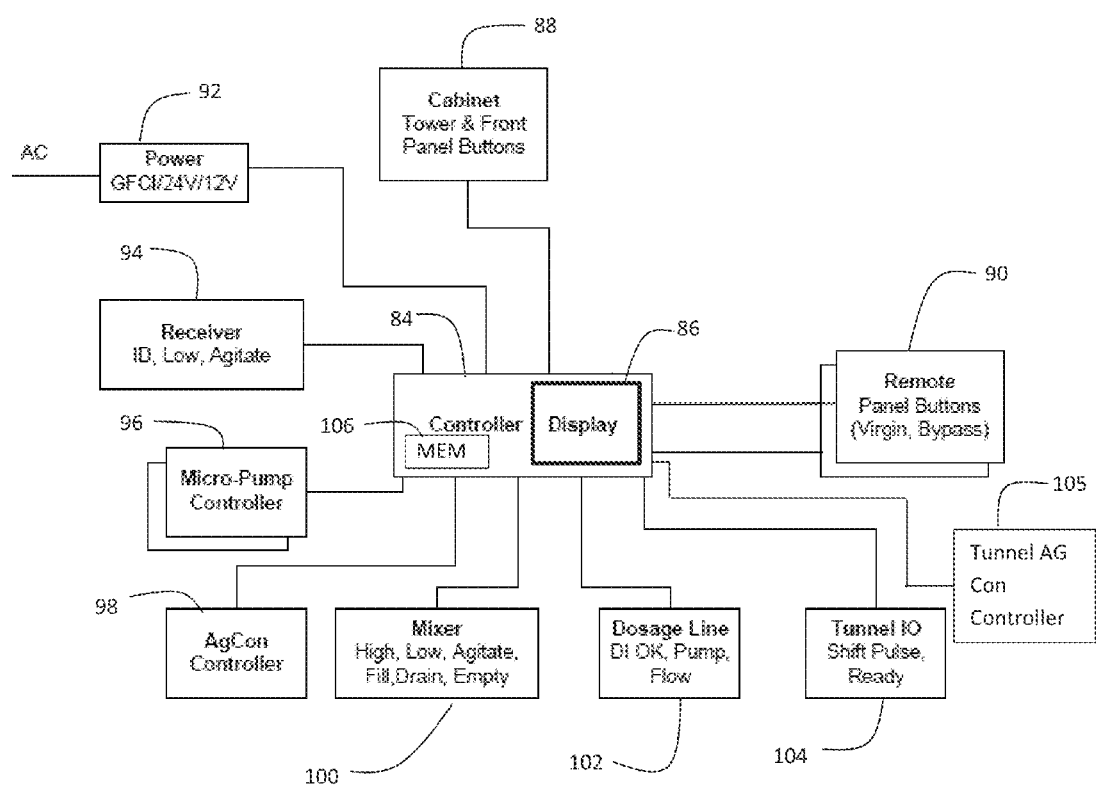
FIG. 3 is a block diagram of the electronics module control processes.

The functional operational aspects of the electronics control module 44 are shown in detail in FIG. 3. A system controller 84, which may be a microprocessor or similar device incorporated with the electronics control module 44 mounted in the cabinet 12, and a display 86 for interaction with an operator provide control for the concentrate supply and dilution system. In exemplary embodiments a Arduino Mega single board computer is employed. Alternatively, a laptop computer or similar device may be employed which incorporates one or both of the system controller and display requirements. A panel with control buttons 88 is employed on the cabinet 12 for input by the operator for control of various aspects of the system operation such as initial high concentration dosing, calibration, normal concentration dosing or system bypass for manual dosing. Another input could be the mass of the textiles which the software uses to calculate the final mg/kg of Ag+ needed. In various embodiments the control buttons may be incorporated on the display as a touch screen or for alternative employing a laptop or other computer, the keyboard may provide the control button functions. A remote panel 90 at an alternative location interfacing with the system controller 84 under wired or wireless connection may also be supplied for remote control input. A power supply 92 provides power conversion from standard AC line input to DC voltages for solenoid operation and microprocessor and display power. A receiver control 94 incorporates hardware for processing of input from the identification element 82, the low level sensor 80 and for operation of the magnetic driver 78 and associated mixing spinner 76. A micro-pump controller 96 receives instructions from associated software routines in the system controller 84 for operation of the metering pump 72 and a silver concentrate controller 98 connected to the conductivity measurement probe 32, which interprets conductivity measurements and translates them into silver concentration readings so that the system controller 84 may interactively control addition of silver concentrate from the canister 50 to the addition column 14. An addition column functional I/O grouping 100 incorporates hardware and software routines in the system controller for operation of the functions of the addition column 14 including operation of the mixer 30, detection of overflow, dose and reserve fill quantities through connection to level probes 36a and 36b and 36c. The exemplary system described herein has no hardware component for empty level control; rather it is determined in software (timing based functions) in reference to extended periods of inactivity by the reserve level sensor. At the point of inactivity, the system drains, resets and fills the column 14 with DI and looks for the reserve level sensor 36c to trigger. If no fill is detected, an alarm signals. The column is not drained until empty during normal operation in order to maintain wetting of the concentration probe 32. Dry to fill could result in air bubble formation on the surface of the concentration probe 32, leading to false readings. Fill of the addition column by control of solenoid valve 18 is accomplished by the addition column controller. Flushing of the additional column to the commercial washer system is accomplished by a dosage line functional grouping 102 which controls operation of solenoid valve 24 and the dosing pump 26 upon instruction from the system controller 84. A commercial washer system interface 104 receives data from the commercial washer system, as will be described subsequently, for status to allow proper timing and operation of the flushing of the addition column, lines flush and DI water fill input. A second silver concentrate controller 105 receives input from a silver concentrate sensor in the commercial washer system for communication to the system controller 84 which may then adjust delivery of concentrate and relative dilution of the concentration to obtain a desired ultimate concentration in the commercial wash system. A memory 106 is employed by the controller for software routines storage and random access memory for process and sequence data.

Figure 4:
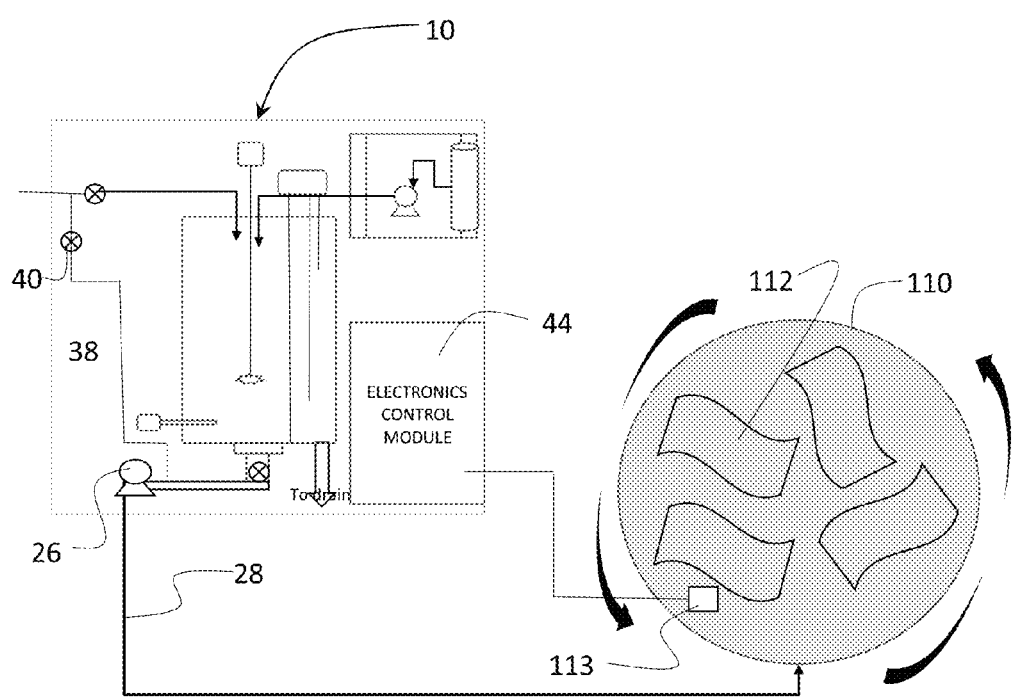
FIG. 4 is a block diagram of the elements for antimicrobial agent infusion into fabrics.

Infusion of the antimicrobial silver concentrate into textiles is accomplished using system elements as shown in FIG. 4. Silver ions are naturally antimicrobial. When treated with silver, textiles exhibit antimicrobial efficacy and fight off bacteria fungi and virus. In order to produce antimicrobial characteristics, the linen must be treated with and maintain a certain minimum silver content, across the entire textile, which can be specified and measured in terms of mg Ag per kg linen. The silver content can be measured with inductively coupled plasma (ICP) down to 0.25 mg Ag per kg textile. Silver-treated linen must maintain at least 0.75 mg Ag per kg textile to achieve antimicrobial efficacy. As the content of silver increases relative to textile weight, the antimicrobial efficacy increases. For example, 0.75 mg Ag/kg may kill 99.9% *S. aureus* 24 hours, while 3 mg Ag/kg may kill 99.9% *S. aureus* in 30 minutes. As the surface area of different textiles vary, an additional amount of Ag may be needed. However, metallic ion concentration at a maximum of 100 mg Ag per 1 kg textiles is introduced by the system into the basin.

During the treatment process, silver attaches to linen via electrostatic dipole interactions. The positive charge from the silver ions is attracted to the slight-negative dipole on the polymer backbone of linen fibers. For example, cotton sheets are composed of cellulose monomers which contain a number of oxygen molecules which are electronegative. The electronegativity of the oxygen molecules are a target active site for the positively charged silver ion. A similar interaction is observed between silver ions and the "ester" group on polyester linen. The ester is composed of a carbonyl oxygen (carbon double bonded and singly bonded to oxygen). Through use of deionized water in the present system, removal of contaminants creates a greater probability that silver ions will affix to reactive bonding sites on the linen's polymer chains as opposed to cationic contaminants and similarly, reduction of the probability of anionic contaminant's reactions to silver ions. Also the higher concentration of silver ions in solution creates driving force for the ions to bond with electronegative dipoles.

Affinity of silver to textile's electronegatively charged dipoles is high. Thus, highly concentrated solution will result in unevenly coated silver ions on the fabric, as a result of 'first come, first serve' behavior of reactive dipole-to-linen attraction. To overcome this, a standing bath of pure DI water is created and clean textiles are submerged in the bath. Agitation is then initiated and ionic silver solution is administered over the duration of at least 20 seconds of agitation of the bath to evenly coat submerged linen; additional agitation of up to 2 minutes following silver administration will help smooth out uniformity of silver across the treated textiles. Submersion forces a minimum volume:mass ratio between DI+Ag solution and textile material, regardless of treatment basin geometry. In an exemplary embodiment, the basin moves relative to the textile load, causing the textile shape to modulate, forcing the fluids to completely exchange throughout the volume such as in a rotating drum.

As seen in FIG. 4, a wash basin 110, which may be a standard rotating wash tub of a commercial washing system, receives textiles 112. As defined herein the wash basin may be a single basin for use in detergent addition cycles and rinse cycles or may be separate dedicated detergent or rinse cycle basins and the dosing of antimicrobial agent may be in either a detergent addition cycle or a rinse cycle to implement the treatment. By operation of the solenoid valve 40 in the concentrate supply and dilution system 10 to supply DI water through DI flush 38 and pump 26 to the outlet 28 wash basin 110 is filled with DI water to establish the standing bath for contained textiles 112. Agitation of the wash basin 110 is then initiated and the desired ionic silver solution concentration is delivered from the concentrate supply and dilution system by operation of solenoid dosing valve 24 and dosing pump 26. The dosing pump 26 is variable speed or is of fixed speed and is sized to provide full dosing of the ionic silver solution concentration from the addition column 14 over the desired dosing period for even coating of the submerged textiles 112. A second silver concentration sensor 113 may be inserted in the commercial wash basin or tunnel for measurement of actual dosed concentration. Output of the sensor 113 is provided to the second silver concentrate controller 105 for communication to the electronics control module as previously described (individual connections between control and monitoring components and the electronics control module are not shown to allow clarity in the drawing). Different linen compositions may require modified dosing periods or concentrations to maximize the efficacy of the antimicrobial action. The system controller in the electronics control module may be programmed to accommodate varying linen compositions through identified input from the user interface (UI) for a particular linen type with predetermined dosing period and concentration settings. Alternatively, manual input through the UI may be employed for concentration and/or dosing period to accommodate required alternative linen settings as described subsequently.

Retention characteristics of silver ions in textiles during multiple wash cycles has demonstrated that an initial treatment with higher silver ion concentration, approximately a factor of 4 over standard treatment concentrations provides a higher starting point to maintain silver ion retention in the textiles for increased efficacy of the antimicrobial action in the textiles. The ultimate asymptotic level of silver ion content in textile is roughly a factor of 4 over the standard treatment on mass silver per mass textile basis.

Figure 5:
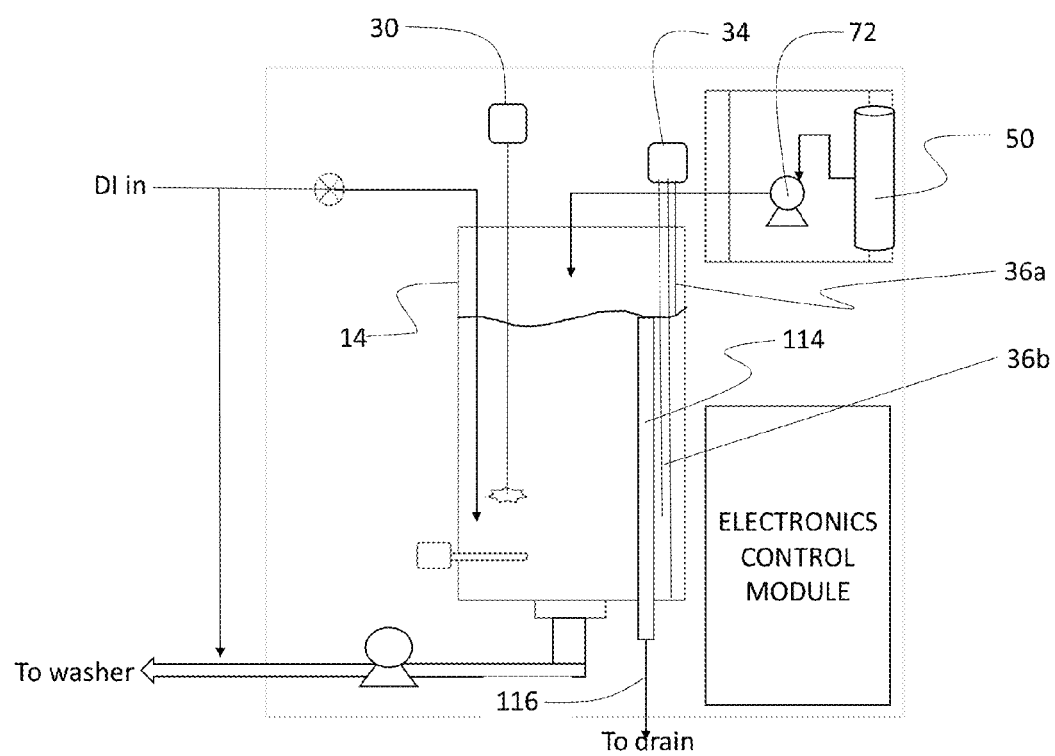
FIG. 5 is a block diagram of a second embodiment of the concentrate supply and dilution system.
Figure 6:
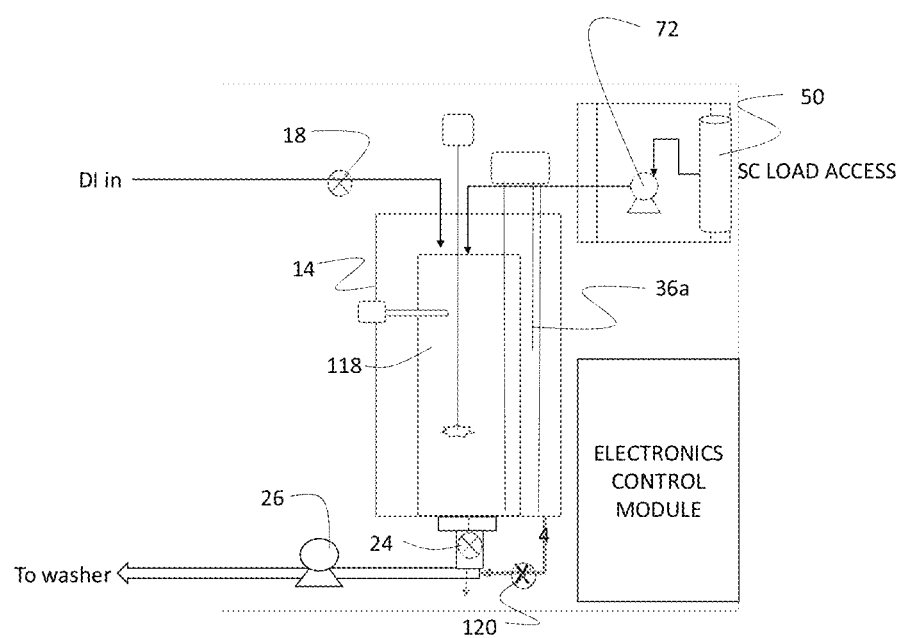
FIG. 6 is a block diagram of a third embodiment of the concentrate supply and dilution system.

For additional control of diluted concentration of the antimicrobial silver ion concentrate in the addition column 14 supplemental elements may be added as shown in FIGS. 5 and 6. In FIG. 5, a drain standpipe 114 having an entrance level consistent with the high level sensor 36a and an exit to a drain 116 is provided in the addition column 14. During addition of DI water to the addition column using solenoid valve 18 high level sensor 36a provides control input to the electronics control module 44 to close solenoid valve 18 upon DI water fill to that level (individual connections between control and monitoring components and the electronics control module are not shown to allow clarity in the drawing). However, any excess fill due to delay or hysteresis in closing of the valve is avoided since any overflow will be directed through the drain standpipe. An exact quantity of DI water is then present in the addition column 14 for concentrate metering by metering pump 72 from the canister 50 into the addition column. Mixing and concentration measurement may then be accomplished as previously described for the embodiment of FIG. 1.

Similarly in FIG. 6, addition column 14 incorporates a precision volume insert 118 into which DI water is introduced through supply solenoid valve 18. The DI water in the precision volume insert 118 is allowed to overflow into the addition column 14 until an overflow level indicated by high level sensor 36a is reached. The level indication from the high level sensor 36a to the electronics control module 44 results in closing of solenoid valve 18 (individual connections between control and monitoring components and the electronics control module are not shown to allow clarity in the drawing). An exact quantity of DI water is then present in the precision volume insert 118 for concentrate metering by metering pump 72 from the canister 50 directly into the precision volume insert in the addition column. Mixing and concentration measurement may then be accomplished as previously described for the embodiment of FIG. 1. Upon depletion of the precision metering column through solenoid valve 24 and dosing pump 26, overflow present in the addition column may be released through solenoid valve 120 through dosing pump 26 to flush the inlet line 28 into the washer system to obtain a complete accurate dose of the diluted concentrate from the addition column without any additional diluted antimicrobial agent.

Figure 7:
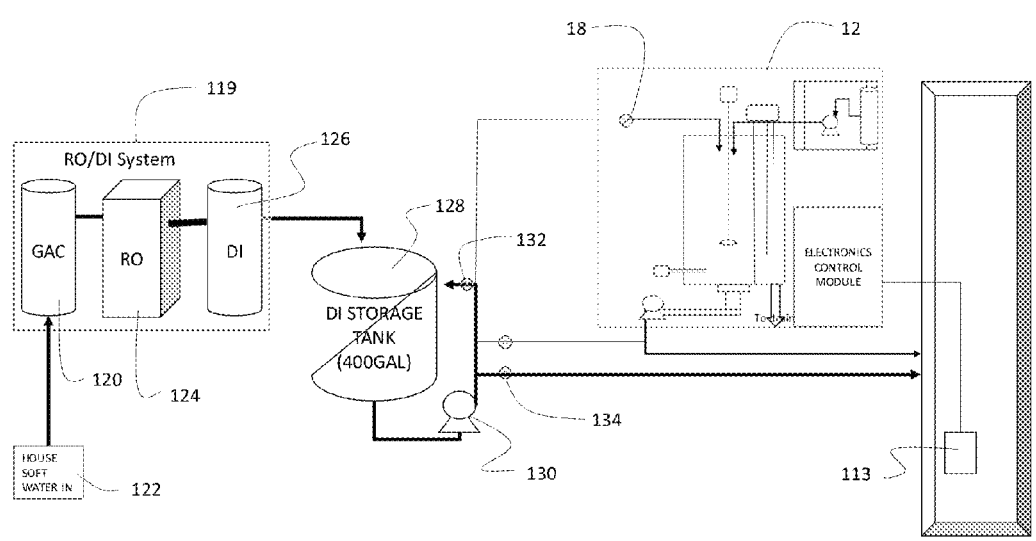
FIG. 7 is a block diagram of a high flow capacity system for antimicrobial concentrate supply; and, FIG. 8 is a block diagram of a direct flow concentrate additional embodiment.

A high flow rate washer basin fill system employing the concentrate supply and dilution system is shown in FIG. 7. A treatment system 119 employs agranulated activated carbon (GAC) filter 120 receiving water from the house soft water source 122. Water drawn from the GAC flows through a reverse osmosis (RO) filter 124 and into a deionizing (DI) mixed-bed resin 126 from which process DI water is provided to a storage tank 128, for exemplary embodiments a 400 gal tank, from which DI water is supplied through high volume pump 130. Treating water from the house soft water source is accomplished to control total dissolved solids (TDS) to a level <300TDS. A return flow through solenoid valve 132 allows flow rate and pressure to be maintained without pump startup delay. DI water may then be supplied from the pump 130 directly to the tunnel washer 134 or to the concentrate supply and dilution system 12 through solenoid valve 18 for introduction of antimicrobial agent as previously described.

Figure 8:
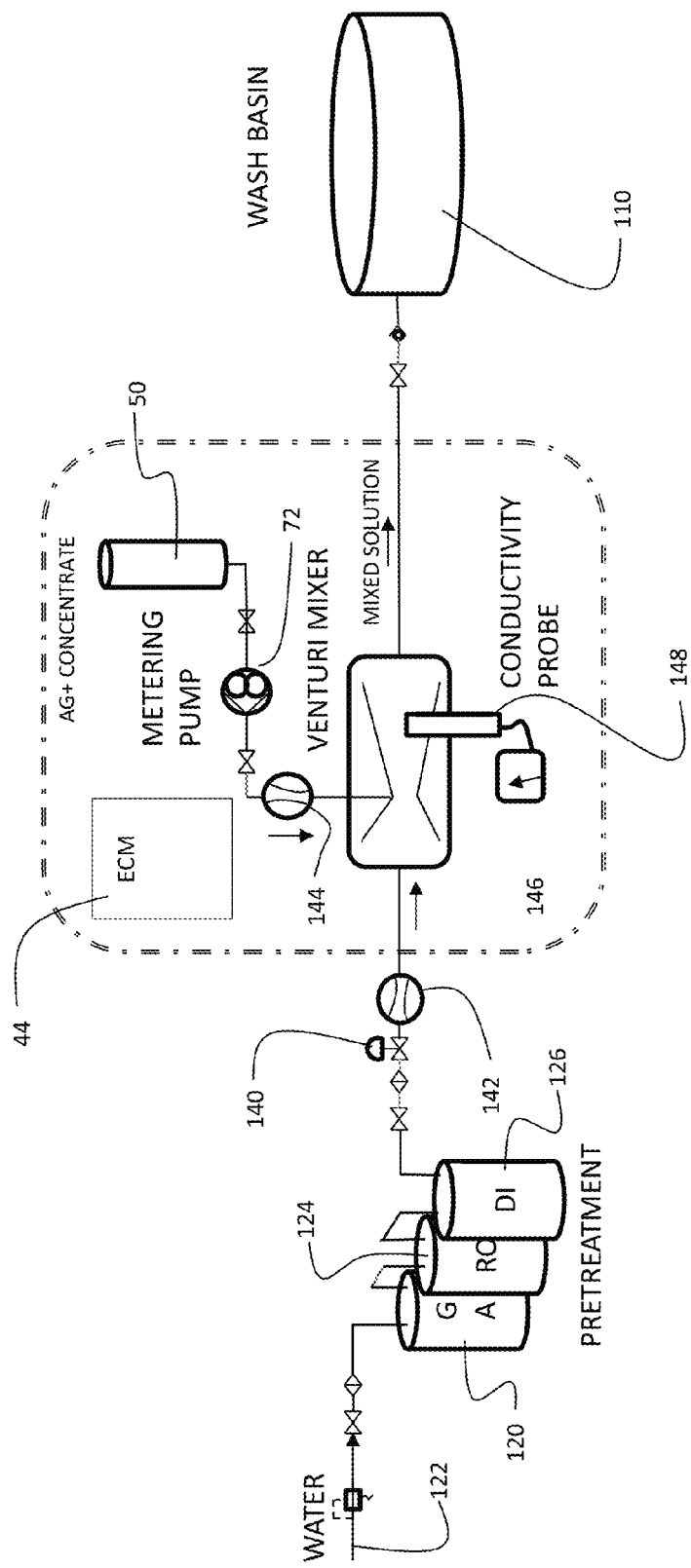

As an alternative to use of a dilution reservoir or addition column, antimicrobial silver concentrate may be mixed directly into a water supply stream as shown in FIG. 8. As for the embodiment described with respect to FIG. 7, treatment of a house water supply is provided by a treatment system employing a granulated activated carbon (GAC) filter 120 receiving water from the house soft water source 122. Water drawn from the GAC flows through a reverse osmosis (RO) filter 124 and into a deionizing (DI) mixed-bed resin 126 from which process DI water is provided through a control valve 140 and a flow meter 142 connected to the electronics control module 44 for control and monitoring (individual connections between control and monitoring components and the electronics control module are not shown to allow clarity in the drawing). As previously described for the prior systems, concentrate from canister 50 is provided through metering pump 72. A second flow meter 144 for confirmation of the flow through the metering pump may be employed. Flow from the control valve 140 and metering pump 72 are combined in a venturi mixer 146 for direct mixing of the concentrate into the incoming water flow. A conductivity probe 148 provides actual resulting concentration to the electronics control module 44 for control of the metering pump 72 and control valve 140 to obtain desired concentration in the mixed water solution provided from the venturi mixer to the wash basin 110. Control by the electronics control module of the metering pump 72 is employed to provide the desired dosing time as a portion of a fill cycle for the wash basin through the control valve 140 with associated control of agitation of the wash basin as previously described. Alternately, the output of the venture mixer may be used with a holding column and then dosed as previously described.

Standard operation of the concentrate supply and dilution system has been previously described. The system control capability provided by the electronics control module 44 allows great flexibility in operation of the system to provide various process features. Normal operations include, column flush, column calibration, metering pump calibration, measurement probe calibration, canister new/replacement, metering pump purge, flush dosing line, initial concentration addition full cycle operation, standard concentration addition full cycle operation and manual addition for standard, initial and custom processes. The electronics control module with the associated controller and display may provide alarms, data recording and other operational screen displays.

A column flush is accomplished by opening DI fill solenoid valve 18 to fill the addition column 14 to high level sensor 36a. Drain valve 42 is then opened to drain the addition column 14 and then closed. This fill and drain process is repeated two times. The DI fill solenoid valve 18 is then controlled to fill to the addition column 14 to the high level sensor 36a. The operator then provides a manual input to acknowledge that the dosing line 28 is configured for flush. Dosing valve 24 is then opened and dosing pump 26 is turned on for a predetermined time for complete flush of the line 28 and/or washing system. Dosing pump 26 is then turned off and dosing valve 24 is closed. The DI flush valve 40 is then opened and dosing pump 26 is activated for a predetermined time for DI flush. The dosing pump 26 is then turned off and DI flush valve 40 is closed. The display then shows a task complete message.

Column calibration is accomplished for the addition column by metering a predetermined quantity of antimicrobial concentrate from the canister 50 into the addition column 14 to ensure conductivity measurement by the level sensing probes 36a, 36b, 36c. Verification of reservoir volume may be accomplished starting with solution absent from the column. Verification of the reservoir volume is accomplished with each test cycle and step in the cycle prompted from the user interface (UI) provided by the display 86 and control panel buttons 88 as previously described. DI fill solenoid 18 is opened until water level contact with the dose level probe 36b occurs. Drain valve 42 is opened until the reservoir level probe 36c is disengaged. Dosing line 28 is temporarily routed into a volume measurement device such as a graduated cylinder. Dosing valve 24 is opened and dosing pump 26 turned on for 1 minute to ensure all solution is pumped out of the column as verified by the operator. This process is repeated adjusting pump timing and reservoir level probe location until target volume is achieved. Dosing valve 24 is then closed and dosing pump 26 turned off. Complete reservoir volume is measured by the fluid in the graduated cylinder.

Verification of delivery volume may be accomplished at the conclusion of the reservoir volume test cycle. Verification of the delivery volume is then accomplished with each test cycle and step in the cycle prompted from the user interface (UI) provided by the display 86 and control panel buttons 88 as previously described. DI fill solenoid 18 is opened until water level contact with the dose level probe 36a occurs. Dosing line 28 is temporarily routed into a volume measurement device such as a graduated cylinder. Dosing solenoid valve 24 is opened and dosing pump 26 turned on. Dosing valve 24 is closed and pump 26 turned off when low level probe 36b is reached. This process is repeated adjusting pump timing and low level probe location until target volume is achieved. The process is then repeat two times for confirmation when target volume is achieved Metering pump calibration is accomplished by temporarily routing outlet conduit 74 into an analytical balance. Manual setting is enabled and/or engagement of standard pump rate at the UI with fixed RPM on the metering pump 72 for Initial and Standard addition. Selectable run times are enabled in increments of 10 sec. "Initial" or "Standard" is selected for pump run mode. The metering pump is then activated for the pre-set time and delivery quantity confirmed on the analytical balance. A prompt for repeat may be provided or the UI may return to home screen.

Conductivity measurement probe calibration is accomplished by occasional auto-calibration and occasional manual calibration.

Canister new/replacement is accomplished as prompted by the UI. In an exemplary embodiment, a yellow alarm is activated when the canister 50 reaches a low level designation by the level sensing device 80, (for example indicating one day of operation remaining) A red alarm is activated and a system stop (system deactivation) when the canister reaches 200 addition cycles after the low level alarm. Installation of a canister 50 into the receiver 52 is accomplished by switching the system to OFF or HOLD. The old canister removed and the new canister is connected to the receiver plumbing and electronics. The system acknowledges the new canister, (manual button or auto barcode/sensor or on-board memory device 82 read as previously described) and is then ready to operate. Separately, a small additional volume in 202 is sized sufficiently to allow continuous use while changing the bottle. For example, if 1 mL were used per cycle, the extra volume would be 30 mL to allow 30 additional minutes to operate.

Metering pump purge is accomplished when necessary by opening column drain valve 42 and turning on the metering pump for 30 seconds. The metering pump is then turned off. An addition column flush is instituted with drain valve 42 closed by opening DI fill valve 18 until the overflow probe 36a is activated then opening drain valve 42. The addition column flush is then repeated two times.

Flush dosing line is accomplished by opening the DI dosing line flush valve 40 and turning on the dosing pump 26 for a predetermined time based on line volume. The DI dosing line flush valve 40 is then closed and the dosing pump turned off.

Conductivity level probes 36a, 36b and 36c may not "see" DI water on first fill of the addition column that has no residual Ag+ due to lack of conductance. A supplemental float indicator for high level indication may be employed and a first fill to trigger the float indicator with a metering pump addition that will obtain Ag+ concentration the same as an initial dose accomplished. The addition column may then be drained to the low level probe 36b before beginning normal cycles.

Operational application requires that the system is capable of creating SC solution deliveries in either Standard or Initial dose concentrations from a variety of pre-existing solution concentration states. The system is capable of producing Initial or Standard concentration SC solutions from concentrations of 0 concentration, Standard concentration or Initial concentration states as shown in Table 1 below.

TABLE 1

| Addition type | Dosing Scenario | Target Delivery Volume |
| --- | --- | --- |
| 4 | Startup - Std | 643 |
| 5 | Startup - Initial | 1930 |
| 0 | Std to Std | 429 |
| 1 | Std to Initial | 1715 |
| 2 | Initial to Std | 0 |
| 3 | Initial to Initial | 1286 |

In the following example, the Initial SC solution is created from a 0 concentration state. Upon receipt of a cycle signal from the washer system interface 104 in the electronics control module initial linen dose addition is accomplished by opening the addition column DI fill solenoid valve 18 is opened for approximately 10 sec until the reservoir level probe 36c is triggered. Metered addition of concentrate from the canister 50 is accomplished with precision pump 72 into the addition column (<60 sec) providing an addition of 1930 uL of concentrate. Simultaneously, DI fill solenoid valve 18 is opened for approximately 10 sec until the dose level probe 36a is triggered. The conductance measurement probe 32 is de-energized and the mixer 30 energized for 30 seconds. After 20 sec of mixing, the conductance measurement probe 32 is energized and conductance of the diluted concentration is measured during final 10 sec. Upon confirmation of proper concentration, the addition column product is dosed to the washer by opening dosing solenoid valve 24 and turning on dosing pump 26 until reservoir level probe 36b is dis-engaged from solution. As previously described, the dosing pump is sized to provide the dose within a predetermined dosing period for optimum silver uptake in the textiles. The dosing valve 24 is then closed and dosing pump 26 turned off. The dosing pump and line are then flushed to extract all of the Ag intended to be used in the washer by opening DI dosing line flush valve 40 (based on line volume) and turning dosing pump 26 on (based on line volume). The DI dosing line flush valve 40 is then closed and the dosing pump 26 turned off.

For standard silver ion concentration addition from a standard reservoir concentration state, DI fill solenoid valve 18 is opened (<10 sec) to fill the addition column until dose level probe is triggered. Simultaneously, metered addition of concentrate from canister 50 is accomplished with precision pump 72 into the addition column (<10 sec) providing an addition of 429 uL of concentrate. The conductance measurement probe 32 is de-energized and the mixer 30 energized for 30 seconds. After 20 sec of mixing, the conductance level probe 32 is energized and conductance of the diluted concentration is measured during final 10 sec. Upon confirmation of proper concentration, the addition column product is dosed to the washer upon receipt of a cycle signal from the washer system interface 104 in the electronics control module by opening dosing solenoid valve 24 and turning on dosing pump 26 until reservoir level probe 36b is dis-engaged from solution. As previously described, the dosing pump is sized to provide the dose within a predetermined dosing period for optimum silver uptake in the textiles. The dosing valve 24 is then closed and dosing pump 26 turned off. The dosing pump and line are then flushed to washer by opening DI dosing line flush valve 40 (based on line volume) and turning dosing pump 26 on (based on line volume). The DI dosing line flush valve 40 is then closed and the dosing pump 26 turned off.

For the concentrate supply and dilution system as described with respect to FIG. 1 the ullage remaining in the addition column, i.e. the volume of fluid present between the reservoir level probe 36*b* volume and the empty column, requires modification of the concentrate addition to achieve desired diluted concentrate properties when shifting between an initial treatment and standard treatment concentrations (as an example 3× dosage for initial and 1× dosage for standard) as previously shown in Table 1. The controller 84 in the electronics control module provides process data sequence storage in memory 106 to allow variation of the added concentrations from the canister to the addition column. For example, if an exemplary system employs an addition column of 1.5 L with an ullage of 0.5 L and a normalized standard concentration level for linen treatment of 1.0, if the system has been running standard concentration fills, the reserve fluid in the ullage will have a volume of 0.5 L with a silver concentration of 1.0 at the conclusion of a 1.01 dose delivered to the wash system. Adding the DI water to the addition column for a full 1.5 L requires the addition of a 1.0 dose of silver yielding a 1.0 concentration level for the entire 1.5 L column. Delivery of a 1.0 dose then leaves the ullage with 0.5 L again at a concentration of 1.0. If an initial concentration dose for treatment of textiles is then desired, starting with an ullage of 0.5 L with a concentration of 1.0 adding the 1.0 L of DI water to the addition column then requires addition of a 4.0 dose of silver to yield the desired 3.0 concentration in the 1.5 L total volume for an initial linen treatment. Upon delivery of the 1.0 liter dose, the ullage now contains 0.5 L with a 3.0 concentration. If an additional initial linen treatment dosage is then desired, the 1.0 L fill of DI into the addition column only requires a 3.0 dose of silver to yield a 3.0 concentration in the 1.5 L volume. However, if a standard treatment is desired after an initial treatment dose, the 0.5 L ullage with a 3.0 concentration upon filing to the 1.5 L volume requires a 0.0 dose of silver achieve the desired 1.0 concentration. Upon delivery of a 1.0 L dose to the washer, the ullage again has a 1.0 concentration remaining.

Manual addition of desired diluted concentrate to the commercial washer system may be accomplished through the UI for either the standard or initial concentration levels. In exemplary systems, the UI may additionally provide the ability to alter metering pump activation times for custom concentration dosing. The system can create any concentration of dose desired by controlled Interaction between concentrate canister and addition column by the electronics module, within the limits of the metering pump resolution. A dose volume is set by the difference in volume defined by volume in the addition column defined by level sensors 36*b* and 36*c*. Responsive to a desired concentration input through the UI, the system controller in the electronics module calculates the amount of concentrate required to produce the desired diluted concentration in the addition column. Operation of the metering pump is controlled by the electronics module to supply that amount of concentrate. Feedback to the system controller from the level sensors and concentration probe during DI fill and concentrate metering is accomplished to determine if a predetermined dose acceptance criteria is met. If the desired concentration is not met, the system controller may issue an alarm, system dump or system correction. For example, if a low concentration is detected, operation to meter more concentrate into the addition column may be undertaken and re-measurement by the concentration probe. If concentration is too high either add more DI or dump to reserve level and start dose over.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for infusing a metallic ion into a textile comprising:
    determining whether an initial treatment or a standard treatment of the textile is to be performed;
    filling a precision volume insert of an addition column with water until a high level probe is triggered;
    responsive to the high level probe being triggered, delivering a concentrated solution of metallic ion from a concentrated supply to the precision volume insert of the addition column;
    receiving the concentrated solution from the concentrated supply in the precision volume insert of the addition column, wherein a volume of the addition column is greater than a volume of the precision volume insert;
    mixing, in the precision volume insert, the concentrated solution of metallic ion with a supply of water to provide a first solution comprising a first concentration of metallic ion;
    measuring in the precision volume insert the first concentration of the metallic ion in the first solution;
    controlling, based on the measurement of the first concentration, an addition of the concentrated solution of metallic ion from the concentrated supply to the precision volume insert to provide a diluted solution having a predetermined concentration of the metallic ion, wherein the predetermined concentration is based on the determining whether the initial treatment or the standard treatment is to be performed, wherein the predetermined concentration is higher for the initial treatment than the standard treatment of the textile;
    receiving the textile in a basin containing water;
    transferring, from the precision volume insert to the basin, at least a portion of the diluted solution until a dose-level probe disengages from the diluted solution in the precision volume insert, wherein the at least the portion of the diluted solution having the predetermined concentration of the metallic ion combines with the water in the basin to provide a second solution having a second concentration of metallic ion in the basin, wherein transferring the at least the portion of the diluted solution comprises varying a dosing rate during a dosing period; and
    agitating, in the basin, the textile while submerged in the second solution to infuse the textile with the metallic ion.

2. The method as defined in claim 1 wherein the predetermined concentration of the initial treatment is at least about four times higher than the predetermined concentration of the standard treatment.

3. The method as defined in claim 1 wherein the basin is a tunnel washer.

4. The method as defined in claim 1 further comprising:
    washing the textile using a detergent to clean the textile; and
    after washing the textile, submerging the textile in the basin prior to transferring the at least a portion of the diluted solution to the basin.

5. The method as defined in claim 1 wherein varying the dosing rate over the dosing period is configured to facilitate uniform uptake of the metallic ion in the textile.

6. The method as defined in claim 1 further comprising determining the dosing rate and the dosing period based on a mass of a textile load in the basin.

7. The method as defined in claim 1 wherein the dosing rate is based on a mass of the textile.

8. The method as defined in claim 1 wherein the metallic ion is a silver ion and the second concentration results in a maximum of 100 mg Ag per 1 kg of textiles to be treated.

9. The method of claim 1 wherein the metallic ion is a silver ion.

10. The method of claim 1, wherein the dosing period is approximately 20 seconds to approximately 30 seconds.

11. The method of claim 1, further comprising treating the water supplied to the precision volume insert by deionization.

12. The method of claim 11, further comprising treating the water in the basin by at least one of deionization and reverse osmosis.

13. The method of claim 1, wherein the predetermined concentration achieves an uptake of at least 0.75 mg of the metallic ion per kg of the textile for the initial treatment and maintains the uptake of at least 0.75 mg of metallic ion per kg of the textile for each standard treatment, which is performed after the initial treatment.

14. A method for infusing a metallic ion into textiles comprising:
   filling an addition column with deionized water until a high level probe is triggered;
   responsive to the high level probe being triggered, metering a high ion concentrate of a metallic ion from a metallic ion supply canister into the addition column with a metering pump;
   receiving the high ion concentrate from the metallic ion supply canister in a precision volume insert of the addition column, wherein a volume of the addition column is greater than a volume of the precision volume insert;
   mixing, using a mixer, the deionized water and the high ion concentrate in the precision volume insert of the addition column to form a diluted concentrate; and,
   administering, using a dosing pump, a dose of the diluted concentrate from the precision volume insert to a washing system until a dose-level probe disengages from the diluted concentrate in the precision volume insert,
   wherein the washing system includes the textiles such that administering the dose of the diluted concentrate to the washing system causes the textiles in the washing system to be infused with the metallic ion, and
   wherein administering the dose comprises varying a dosing rate during a dosing period.

15. The method as defined in claim 14 further comprising dissolving a silver metallic compound into a solution in the metallic ion supply canister.

16. The method of claim 14, wherein the step of filling the addition column comprises filling the precision volume insert to a predetermined level with the deionized water.

17. The method as defined in claim 14 wherein the step of administering the diluted concentrate dose further comprises:
   filling a wash basin with process water to establish a standing bath for textiles;
   agitating the process water in the wash basin; and,
   while agitating, pumping the dose of the diluted concentrate from the precision volume insert to the wash basin.

18. The method as defined in claim 14 wherein the dosing period is approximately 20-30 seconds.

19. The method of claim 14, further comprising:
   after mixing the deionized water and the high ion concentrate, measuring, by a conductance probe, the concentration of the metallic ion in the diluted concentrate;
   determining, based on the measured concentration and by an electronics controls module, additional high ion concentrate needs to be supplied to the precision volume insert to reach a predetermined concentration level for the diluted concentrate; and
   responsive to determining that additional high ion concentration needs to be supplied, metering the additional high ion concentrate from the metallic ion supply canister into the addition column until the concentration measured by the conductance probe reaches the predetermined concentration level for the diluted concentrate.

20. The method of claim 14, further wherein filling the addition column comprises overflowing the deionized water from the precision volume insert into the addition column.

21. The method of claim 14, further comprising, after administering the dose, flushing the dosing pump and a line from the dosing pump to the washing system.

* * * * *